(12) United States Patent
Shima et al.

(10) Patent No.: US 7,785,784 B2
(45) Date of Patent: Aug. 31, 2010

(54) DETECTION OF OLIGONUCLEOTIDES BY DUAL HYBRIDIZATION

(75) Inventors: David T. Shima, Herts (GB); Pericles Calias, Melrose, MA (US); Gregory S. Robinson, Wilmington, MA (US); John P. Wing, Walpole, MA (US); Lori M. Mullin, West Townsend, MA (US); Lillian M. Smith, Lynn, MA (US); Ervin Sinani, Revere, MA (US)

(73) Assignee: Eyetech, Inc., Palm Beach Gardens, FL (US)

( * ) Notice: Subject to any disclaimer, the term of this patent is extended or adjusted under 35 U.S.C. 154(b) by 468 days.

(21) Appl. No.: 11/186,660

(22) Filed: Jul. 21, 2005

(65) Prior Publication Data

US 2007/0178476 A1 Aug. 2, 2007

Related U.S. Application Data

(60) Provisional application No. 60/590,507, filed on Jul. 23, 2004.

(51) Int. Cl.
*C12Q 1/68* (2006.01)
*C07H 21/02* (2006.01)
*C07H 21/04* (2006.01)

(52) U.S. Cl. .......................... 435/6; 536/23.1; 536/24.3
(58) Field of Classification Search .................. 435/6; 536/23.1, 24.3
See application file for complete search history.

(56) References Cited

U.S. PATENT DOCUMENTS

| 5,849,890 | A | * | 12/1998 | Gold et al. ................ 536/23.1 |
| 5,876,924 | A | * | 3/1999 | Zhang et al. ................ 435/5 |
| 5,989,823 | A | * | 11/1999 | Jayasena et al. ............... 435/6 |
| 6,015,674 | A | | 1/2000 | Woudenberg |
| 6,426,335 | B1 | * | 7/2002 | Janjic et al. .................... 514/44 |
| 6,927,024 | B2 | * | 8/2005 | Dodge et al. .................. 435/6 |
| 6,955,901 | B2 | | 10/2005 | Schouten |
| 7,125,681 | B2 | * | 10/2006 | Knuth et al. .............. 435/7.23 |
| 2002/0172946 | A1 | | 11/2002 | Fan |
| 2004/0138163 | A1 | | 7/2004 | McSwiggen |
| 2005/0175708 | A1 | * | 8/2005 | Carrasquillo et al. ....... 424/489 |
| 2006/0030535 | A1 | * | 2/2006 | Healy et al. ................... 514/44 |
| 2006/0121458 | A1 | | 6/2006 | Van Eijk |
| 2006/0167435 | A1 | * | 7/2006 | Adamis et al. .............. 604/500 |
| 2007/0027101 | A1 | * | 2/2007 | Guyer et al. .................. 514/44 |

FOREIGN PATENT DOCUMENTS

| EP | 1130113 | 9/2001 |
| EP | 1319718 | 6/2003 |
| WO | WO 95/30139 | 11/1995 |

OTHER PUBLICATIONS

Li, Dao Ke et al. (1998) International Journal of Oncology, Editorial Academy of the International Journal of Oncology, vol. 12, No. 6, pp. 1391-1396.
Zhang, Lin et al. (2003) Biochemical and Biophysical Research Communications, vol. 303, No. 4, pp. 1169-1178.
International Search Report in PCT/US2005/025966.
Written Opinion of the International Search Authority in PCT/US2005/025966.

* cited by examiner

*Primary Examiner*—Ethan Whisenant
(74) *Attorney, Agent, or Firm*—Mintz Levin Cohn Ferris Glovsky & Popeo P.C.; Ivor R. Elrifi, Esq.

(57) ABSTRACT

The invention provides methods and compositions for detecting and/or quantifying modified nucleic acid oligonucleotides. These methods and compositions are useful for detecting and quantifying diagnostic and/or therapeutic synthetic modified oligonucleotides, such as aptamers, RNAi, siRNA, antisense oligonucleotides or ribozymes in a biological sample.

43 Claims, 10 Drawing Sheets where R is  and n is approximately 450

SEQUENCE LISTING

```
<160> NUMBER OF SEQ ID NOS: 24

<210> SEQ ID NO 1
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)
<223> OTHER INFORMATION: 2'-fluorocytidylic acid
<220> FEATURE:
<221> NAME/KEY: modified_base
<222> LOCATION: (2)..(3)
<223> OTHER INFORMATION: 2'-methoxyguanylic acid
<220> FEATURE:
<221> NAME/KEY: modified_base
<222> LOCATION: (4)..(5)
<223> OTHER INFORMATION: Riboadenylic acid
<220> FEATURE:
<221> NAME/KEY: modified_base
<222> LOCATION: (6)
<223> OTHER INFORMATION: 2'-flourouridylic acid
<220> FEATURE:
<221> NAME/KEY: modified_base
<222> LOCATION: (7)
<223> OTHER INFORMATION: 2'-fluorocytidylic acid
<220> FEATURE:
<221> NAME/KEY: modified_base
<222> LOCATION: (8)
<223> OTHER INFORMATION: 2'-methoxyadenylic acid
<220> FEATURE:
<221> NAME/KEY: modified_base
<222> LOCATION: (9)
<223> OTHER INFORMATION: 2'-methoxyguanylic acid
<220> FEATURE:
<221> NAME/KEY: modified_base
<222> LOCATION: (10)
<223> OTHER INFORMATION: 2'-flourouridylic acid
<220> FEATURE:
<221> NAME/KEY: modified_base
<222> LOCATION: (11)
<223> OTHER INFORMATION: 2'-methoxyguanylic acid
<220> FEATURE:
<221> NAME/KEY: modified_base
<222> LOCATION: (12)..(13)
<223> OTHER INFORMATION: 2'-methoxyadenylic acid
<220> FEATURE:
<221> NAME/KEY: modified_base
<222> LOCATION: (14)
<223> OTHER INFORMATION: 2'-flourouridylic acid
<220> FEATURE:
<221> NAME/KEY: modified_base
<222> LOCATION: (15)
<223> OTHER INFORMATION: 2'-methoxyguanylic acid
<220> FEATURE:
<221> NAME/KEY: modified_base
<222> LOCATION: (16)
<223> OTHER INFORMATION: 2'-fluorocytidylic acid
<220> FEATURE:
<221> NAME/KEY: modified_base
<222> LOCATION: (17)..(18)
<223> OTHER INFORMATION: 2'-flourouridylic acid
<220> FEATURE:
<221> NAME/KEY: modified_base
<222> LOCATION: (19)
<223> OTHER INFORMATION: 2'-methoxyadenylic acid
<220> FEATURE:
<221> NAME/KEY: modified_base
```

```
<222> LOCATION: (20)
<223> OTHER INFORMATION: 2'-flourouridylic acid
<220> FEATURE:
<221> NAME/KEY: modified_base
<222> LOCATION: (21)
<223> OTHER INFORMATION: 2'-methoxyadenylic acid
<220> FEATURE:
<221> NAME/KEY: modified_base
<222> LOCATION: (22)
<223> OTHER INFORMATION: 2'-fluorocytidylic acid
<220> FEATURE:
<221> NAME/KEY: modified_base
<222> LOCATION: (23)
<223> OTHER INFORMATION: 2'-methoxyadenylic acid
<220> FEATURE:
<221> NAME/KEY: modified_base
<222> LOCATION: (24)
<223> OTHER INFORMATION: 2'-flourouridylic acid
<220> FEATURE:
<221> NAME/KEY: modified_base
<222> LOCATION: (25)..(26)
<223> OTHER INFORMATION: 2'-fluorocytidylic acid
<220> FEATURE:
<221> NAME/KEY: modified_base
<222> LOCATION: (27)
<223> OTHER INFORMATION: 2'-methoxyguanylic acid

<400> SEQUENCE: 1
cggaaucagu gaaugcuuau acauccg                                          27

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
acggatgtat aagca                                                       15

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
aaaacggatg tataagca                                                    18

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
aaaacggatg tataagcatt cactgattcc g                                     31

<210> SEQ ID NO 5
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 5
ttcactgatt ccg                                                        13

<210> SEQ ID NO 6
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ttcactgatt ccgagagaac agtgtcacgg ttaaaggata aggaactctt ctggaatgac     60
tttgcgggct gttgacga                                                   78

<210> SEQ ID NO 7
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gagagaacag tgtcacggtt aaaggataag gaactcttct ggaatgactt tgcgggctgt     60
tgacg                                                                 65

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
aaggaactct tctggaatga                                                 20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
aaggaactct tctggaatga                                                 20

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gagaacagtg tcacggttaa agga                                            24

<210> SEQ ID NO 11
<211> LENGTH: 17
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 11
cgtcaacagc ccgcaaa                                                       17

<210> SEQ ID NO 12
<211> LENGTH: 83
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aaactccgtg ggacgagtga tacagtgcca gagcaattgg actacgctaa acggcgtatg         60
gctgaaaaac ggatgtataa gca                                                83

<210> SEQ ID NO 13
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13
ccagagcaat tcgac                                                         15

<210> SEQ ID NO 14
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
ccagagcaat tcgac                                                         15

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ctccgtggga cgagtgatac a                                                  21

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tcagccatac gccgtttagc                                                    20

<210> SEQ ID NO 17
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 17
cacccaagac agcagaaag                                                      19

<210> SEQ ID NO 18
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
uugcacauug cucaguucau acacc                                               25

<210> SEQ ID NO 19
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
gguguaugaa cugagcaaug ugcaa                                               25

<210> SEQ ID NO 20
<211> LENGTH: 12
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 20
aactttctgc tg                                                             12

<210> SEQ ID NO 21
<211> LENGTH: 74
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21
tcttgggtga gagaacagtg tcacggttaa aggataagga actcttctgg aatgactttg         60
cgggctgttg acga                                                           74

<210> SEQ ID NO 22
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 22
aaggtgtatg aactg                                                          15

<210> SEQ ID NO 23
<211> LENGTH: 77
<212> TYPE: DNA
```

-continued

```
<213> ORGANISM: Artificial Sequence
<220> FEATURE:
<223> OTHER INFORMATION: Description of Artificial Sequence: Synthetic
      probe

<400> SEQUENCE: 23
agcaatgtgc aaagagaaca gtgtcacggt taaaggataa ggaactcttc tggaatgact    60
ttgcgggctg ttgacga                                                  77

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
cggaatcagt gaatgcttat acatccgt                                      28
```

US 7,785,784 B2

DETECTION OF OLIGONUCLEOTIDES BY DUAL HYBRIDIZATION

RELATED APPLICATION

This Application claims the benefit of U.S. Provisional Application No. 60/590,507, filed on Jul. 23, 2004. The entire teachings of the above application is incorporated herein by reference.

FIELD OF THE INVENTION

The invention is in the field of oligonucleotide detection. More specifically, the invention relates to methods for detecting or quantifying oligonucleotides in a sample, particularly a synthetic aptamer comprising modified nucleotides in a biological sample.

BACKGROUND OF THE INVENTION

Biologically active synthetic oligonucleotides, including aptamers, antisense oligonucleotides, ribozymes and, more recently, short interfering RNAs (siRNAs), have revolutionized molecular medicine by allowing the direct and specific targeting of individual genes and proteins. The ability to sensitively detect and quantify even minute quantities of such exogenous oligonucleotides in a biological sample will be a critical key to their development as clinically relevant therapeutics and diagnostics.

Aptamers (Gr. Aptus—to fit; meros—part or region) are oligonucleotides that bind with very high specificity and affinity to target molecules, including proteins. Aptamer binding relies on the specific three dimensional conformation of the properly folded oligonucleotide. Aptamers, can be generated against amino acids, drugs, proteins and other molecules. They can be isolated from combinatorial libraries of synthetic nucleic acid by an iterative process of adsorption, recovery, and reamplification. Following selection of a primary RNA oligonucleotide sequence that binds tightly to the target, a number of secondary modifications to the backbone, sugars, and bases, as well as to the 5' and 3' ends of the sequence, may be made in order to optimize the stability and/or antagonist (or agonist) biological activity of the aptamer. For example, aptamer oligonucleotides are frequently modified at 2'-ribo positions (e.g. with 2'-fluro or 2'-O-methyl) to make them more nuclease resistant. In addition, the 3' ends of aptamers are frequently modified with an "inverted T cap" (i.e., addition of -3'dT at the 3' end of the aptamer) to increase nuclease resistance, and the use of such an "inverted T cap" structure at the 5' ends of aptamers has also been described (see, U.S. Appln. Ser. No. 60/493,500). Furthermore, the addition of non-immunogenic, high molecular weight or lipophilic compounds to the 5' end, or other position, to improve nuclease resistance and/or other pharmacokinetic properties, has also been described (see, e.g., U.S. Pat. Nos. 6,011,020, 6,147,024, 6,229,002, 6,426,335, 6,465,188, and 6,582,918). Finally, the addition of soluble, high molecular weight steric groups, such as dextran or polyethylene glycol, to improve the antagonist properties of an aptamer has been described (see U.S. application Ser. No. 11/105,279).

An important problem encountered with the use of modified oligonucleotides in therapeutic applications is confirming the presence and persistence of the modified oligonucleotide in the subject. Although there have been numerous methods for detecting and/or quantifying nucleic acids in a biological sample, the presence of extensive modifications in oligonucleotide aptamers and certain antisense agents, in combination with their relatively short length, makes their detection and quantification difficult. Indeed, some high molecular weight modifications, such as 5'-PEGylation, interfere with certain conventional means of detection. Accordingly, a reliable, sensitive and quantitative method for detecting modified oligonucleotides present in a host sample would be very useful.

SUMMARY OF THE INVENTION

The invention is based, in part, upon the finding of methods that allow for the reliable, sensitive and quantitative detection of modified oligonucleotides. In particular, the invention relates to methods for the reliable, sensitive and quantitative detection of modified oligonucleotides including, but not limited to, 5'-PEGylated therapeutic aptamers, siRNA, RNAi, and antisense nucleic acids in a biological sample obtained from a subject.

In one aspect, the invention provides a method of detecting a target oligonucleotide in a sample by contacting the sample with a first polynucleotide that is complementary to a first portion of the target oligonucleotide, so as to allow hybridization of the first polynucleotide with the target oligonucleotide. In this aspect, the first polynucleotide is joined to a functional tag. The sample is then contacted with a second polynucleotide that is complementary to an adjacent and non-overlapping portion of the target oligonucleotide so as to allow hybridization of the second polynucleotide with the target oligonucleotide. The second polynucleotide includes a detectable label or amplifiable sequence that is substantially non-complementary to the target oligonucleotide. The first and second polynucleotides, which are hybridized adjacently to the target oligonucleotide, are optionally then ligated together to form a ligated hybrid complex. The detectable label or amplifiable sequence of the second polynucleotide in the ligated hybrid complex is then detected by an amplification step, or other means. Detection of the detectable label or amplifiable sequence indicates that the target oligonucleotide is present in the original sample.

In certain embodiments of this aspect of the invention, the method of the invention further includes separating the ligated hybrid complex from the rest of the sample using the tag of the first polynucleotide.

In certain embodiments, the target oligonucleotide is a modified oligonucleotide. In some such embodiments, the modified oligonucleotide has a modified phosphodiester backbone. In other such embodiments, the modified oligonucleotide includes at least one modified phosphodiester linkage, such as a phosphorothioate linkage, a phosphorodithioate linkage, a phosphoramidate linkage, or a phosphonate linkage.

In other useful embodiments, the target oligonucleotide includes at least one ribonucleotide nucleotide residue. In still other such embodiments, the modified oligonucleotide includes a 2'-substituted ribonucleotide, such as a 2'-O-alkyl ribonucleotide, a 2'-halo ribonucleotide, a 2'-O-aryl ribonucleotide, a 2'-O-allyl ribonucleotide or a 2'-amino ribonucleotide. In further embodiments, the modified oligonucleotides includes 2'-halo ribonucleotide that is a 2'-fluro ribonucleotide, a 2'-chloro ribonucleotide, a 2'-bromo ribonucleotide, or a 2'-iodo ribonucleotide. In a further embodiment, the 2'-substituted ribonucleotide is a 2'-fluoro ribonucleotide. In other embodiments, the 2'-substituted ribonucleotide is a 2'-O—$C_{1-6}$ alkyl ribonucleotide substituted with one or more substituents selected from the group consisting of halo, hydroxy, trifluoromethyl, cyano, nitro, acyl, acyloxy, carboxyl, carboxyalkyl, and amino. In particular embodiments, the 2'-substituted ribonucleotide is a 2'-O-methyl ribonucleotide. In further embodiments, the 2'-substituted ribonucleotide is a 2'-4' locked ribonucleotide, such as one having a 2'-O, 4'-C methylene bridge structure. In other embodiments, the 2'-substituted ribonucleotide is a 2'-O-aryl ribonucleotide substituted with one or more substituents, such as a halo, hydroxy, trifluoromethyl, cyano, nitro, acyl, acyloxy, carboxyl, carboxyalkyl or amino group. In still other embodiments, the 2'-substituted ribonucleotide is a 2'-O-allyl ribonucleotide substituted with one or more substituents, such as a halo, hydroxy, trifluoromethyl, cyano, nitro, acyl, acyloxy, carboxyl, carboxyalkyl or amino group.

In further embodiments, the modified oligonucleotide is PEGylated, such as the PEGylated aptamer shown in FIG. 3. In other embodiments, the modified oligonucleotide has a soluble, high molecular weight steric group joined at any position along the oligonucleotide. In certain such embodiments, the soluble, high molecular weight steric group is dextran. In other such embodiments, the soluble, high molecular weight steric group is a polyethylene glycol, a polysaccharide, a glycosaminoglycan, a hyaluronan, an alginate, a polyester, a high molecular weight polyoxyalkylene ether, a polyamide, a polyurethane, a polysiloxane, a polyacrylate, a polyol, a polyvinylpyrrolidone, a polyvinyl alcohol, a polyanhydride, a carboxymethyl cellulose, a cellulose derivative, a Chitosan, a polyadlehyde, or a polyether. In particular such embodiments, the polyester group is a co-block polymeric polyesteric group. In other particular such embodiments, the alignate is an anionic alginate that is provided as a salt with a cationic counter-ion, such as sodium or calcium. In certain embodiments, the soluble high molecular weight steric group is a polymeric composition having a molecular weight of about 20 kDa to about 100 kDa. In other embodiments, the soluble high molecular weight steric group is joined to the oligonucleotide at the 5' end of the modified oligonucleotide. In further embodiments, the soluble high molecular weight steric group is joined to the oligonucleotide at the 3' end of the modified oligonucleotide. In still other such embodiments, the soluble high molecular weight steric group is joined to the oligonucleotide at a position other than the 5' end or 3' end of the aptamer sequence. In still further such embodiments, the soluble high molecular weight steric group is joined to the oligonucleotide at a position such as an exocyclic amino groups on one or more bases, a 5-position of one or more pyrimidine bases, an 8-position of one or more purine bases, an hydroxyl groups of one or more phosphate residues, or an hydroxyl group of one or more ribose groups.

In particular embodiments, the target oligonucleotide is an aptamer, such as a VEGF aptamer (e.g., a VEGF aptamer having the structure:

(SEQ ID NO:1)
PEG-linker-$C_fG_mG_mA_mA_mU_fC_fA_mG_mU_fG_mA_mA_mU_fG_mC_fU_fU_fA_m$ $U_fA_mC_fA_mU_fC_fC_fG_m3'-3'-T_d$.

In further embodiments of this aspect of the invention, the first polynucleotide is a deoxyribonucleotide polynucleotide. In other embodiments, the first polynucleotide is a ribonucleotide polynucleotide. In particular embodiments, the first polynucleotide is a capture probe which includes the sequence ACGGATGTATAAGCA (SEQ ID NO: 2). In particular embodiments, the first polynucleotide has the structure:

5'-Amine-AAAACGGATGTATAAGCA-3' (SEQ ID NO: 3). In other particular embodiments, the first polynucleotide has the structure:

5'-Amine-AAAACGGATGTATAAGCATTCACTGAT-TCCG-3' (SEQ ID NO: 4).

In still further embodiments, the tag is a high affinity ligand or binding partner thereto, such as a hapten, an antibody, a ligand, a ligand-specific receptor, a carbohydrate, or a carbohydrate-binding lectin. In some embodiments, the high affinity ligand, or binding partner thereto, is biotin, avidin or streptavidin. In certain embodiments, the tag includes a magnetic bead.

In further embodiments of this aspect of the invention, the second polynucleotide is a deoxyribonucleotide polynucleotide. In other embodiments, the second polynucleotide is a ribonucleotide polynucleotide. In particular embodiments, the second polynucleotide is a detection probe which includes the sequence TTCACTGATTCCG (SEQ ID NO: 5), such as a second polynucleotide having the structure: 5'-Phos-TTCACTGATTCCGAGAGAACAGTGT-CACGGTTAAAGGATAAGGAACTCTTCT GGAAT-GACTTTGCGGGCTGTTGACGA-3' (SEQ ID NO: 6).

In still further embodiments, the second polynucleotide includes a detectable label that is digoxigenin. In certain such embodiments of the method of the invention, the digoxigenin is detected by an anti-digoxigen antibody. In other embodiments, the second polynucleotide includes an amplifiable sequence that is substantially non-complementary to the target oligonucleotide. In one example of such an amplifiable sequence that is substantially non-complementary to the target oligonucleotide, the sequence:

GAGAGAACAGTGTCACGGTTAAAG-GATAAGGAACTCTTCTGGAATGACTTTG CGGGCT-GTTGACG (SEQ ID NO: 7) is utilized. In particular embodiments, the amplifiable sequence of the second polynucleotide is detected using a polymerase chain reaction amplification step. In certain such embodiments, the polymerase chain reaction amplification step is performed using a fluorescent probe that detects an amplicon amplified by the polymerase chain reaction. In particular such embodiments, the fluorescent probe is a TaqMan® probe, such as the TaqMan® probe having a nucleic acid comprising the sequence: AAG GAA CTC TTC TGG AAT GA (SEQ ID NO: 8). In other particular such embodiments, the fluorescent probe is a TaqMan® probe, such as the TaqMan® probe having the structure:

6FAM-AAG GAA CTC TTC TGG AAT GA-MGBNFQ (SEQ ID NO: 9). In further such embodiments, the amplifiable sequence is amplified using a forward PCR primer having the sequence GAG AAC AGT GTC ACG GTT AAA GGA (SEQ ID NO: 10). In other embodiments, the amplifiable sequence is amplified using a reverse PCR primer having the sequence CGT CAA CAG CCC GCA AA (SEQ ID NO: 11). In still further embodiments, the fluorescent probe is a molecular beacon probe, a Scorpion probe, a TaqMan® probe, or a SYBR Green probe.

In particular embodiments of this aspect of the invention, the detection step utilizes a real-time PCR reaction. In such embodiments, the amount of target oligonucleotide present in the sample is quantitated in a quantitative real-time PCR reaction detection step.

In particular embodiments, the polymerase chain reaction amplification includes about 10 to about 40 cycles.

In some embodiments, the first polynucleotide hybridizes to a 3' portion of the target oligonucleotide relative to the portion of the target oligonucleotide that the second polynucleotide hybridizes to. In other embodiments, the first polynucleotide hybridizes to a 5' portion of the target oligonucleotide relative to the portion of the target oligonucleotide to which the second polynucleotide hybridizes. In certain embodiments, the first and second polynucleotide hybridize to adjacent, non-abutting sequences of the target oligonucleotide, and the 3' end of the adjacent but non-abutting polynucleotide is extended using a polymerase so that the first and second polynucleotides are thereby made to be abutting. In certain such embodiments, the polymerase utilized to extend the non-abutting polynucleotide has substantially no net 3' to 5' exonuclease activity and the resulting abutted polynucleotides are ligatable. In still further embodiments, the step of ligating the first and second polynucleotides is performed by contacting the adjacently hybridized polynucleotides with a DNA ligase. In other embodiments, the step of ligating the first and second polynucleotides is performed by contacting the adjacently hybridized polynucleotides with an RNA ligase (e.g. a T4 RNA ligase).

In particular embodiments of this aspect of the invention, the ligated hybrid complex is separated from the rest of the sample using the tag of the first polynucleotide. In certain such embodiments, the tag involves a biotin-streptavidin complex immobilized on a plastic dish. In other such embodiments, the tag that is utilized includes an insoluble substrate, such as a magnetic bead or agarose. In particular embodiments, separation of the ligated hybrid complex from the rest of the sample is achieved by washing the insoluble substrate.

In another useful aspect, the invention provides a method of quantifying an aptamer in a biological sample from a subject. By this method of the invention, the biological sample is first contacted with a capture probe that is complementary to a first portion of the aptamer so as to allow hybridization of the capture probe with the aptamer. The capture probe is joined to a tag. In the next step, the sample is contacted with a detection probe that is complementary to an adjacent abutting, but non-overlapping, portion of the aptamer so as to allow hybridization of the detection probe with the aptamer, the detection probe having an amplifiable sequence that is substantially non-complementary to the aptamer. The capture probe and detection probe, hybridized adjacently to the aptamer, are optionally then ligated together to form a ligated hybrid complex. The hybrid complex is then separated from the rest of the sample using the tag that is joined to the capture probe. The amplifiable sequence of the detection probe present in the hybrid complex is then quantified. By this aspect of the invention, the amount of amplifiable sequence of the detection probe in the hybrid complex corresponds to the amount of aptamer in the biological sample. Accordingly, this method of the invention provides a means for quantifying the amount of aptamer present in the original biological sample from the subject.

In another useful aspect, the invention provides a method of quantifying a nucleic acid using a dual hybridization assay as described above wherein the first polynucleotide comprises a further amplifiable sequence. The first polynucleotide comprising a further amplifiable sequence is useful as a quality control (QC) capture primer ("QC probe"). This aspect of the present invention can be used to better understand the performance of the PCR Dual Hybridization assay.

In one embodiment, the QC capture primer comprises a VEGF aptamer hybridizing sequence: ACGGATGTATAAGCA (SEQ ID NO: 2).

In one embodiment, the QC capture primer comprises the sequence: Amino-AAA CTC CGT GGG ACG AGT GAT ACA GTG CCA GAG CAA TTG GAC TAC GCT AAA CGG CGT ATG GCT GAA AAA CGG ATG TAT AAG CA (SEQ ID NO: 12).

This capture primer is detectable by a TaqMan® probe having the sequence CCA GAG CAA TTC GAC (SEQ ID NO: 13) IN one embodiment, the capture primer is detectable by a TaqMan® probe having the structure 6FAM-CCA GAG CAA TTC GAC-MGBNFQ (SEQ ID NO: 14) and primers of the sequence CTC CGT GGG ACG AGT GAT ACA (SEQ ID NO: 15; forward primer) and TCA GCC ATA CGC CGT TTA GC (SEQ ID NO: 16; reverse primer).

Use of a QC capture primer has several advantages. One advantage of using the QC capture primer is the ability to determine the amount of capture primers covalently bound to the magnetic bead. This is done by performing RT-PCR (Taqman®) on a sample of a QC capture primer-coated magnetic beads after the coating process and extrapolating the Ct value off of a standard curve generated by detecting known quantities of the QC capture primer in solution.

Another advantage of using the QC capture primer is the ability to determine the relative amount of magnetic beads carried through the sample wash steps (e.g., Kingfisher based wash steps). This can determine the robustness and reproducibility of the assay. In one embodiment, after the PCR Dual Hybridization process, 4 µL of magnetic beads are be detected by Taqman, by using the QC capture primer Taqman probe and primer set (see Example 4). This Ct value is extrapolated off of a standard curve generated by detecting free capture primer in solution using the same Taqman primers and probe.

Another advantage of using the QC capture primer is the ability to determine the percent of hybridized sample nucleic acid (e.g., pegaptanib). In one embodiment, this is done by extrapolating the Ct value from a pegaptanib (Macugen®) sample off of a free detection primer standard curve. This curve is generated by Taqman detection of the detection primer. The percent of hybridized Macugen can be calculated due to the 1:1 ration of detection primer hybridized to pegaptanib (See FIG. 2).

In a further aspect, the invention provides kits for detecting a VEGF aptamer in a sample. Such kits may include: a capture probe, such as a capture probe that includes the VEGF aptamer-hybridizing sequence: ACGGATGTATAAGCA (SEQ ID NO: 2); a detection probe, such as a detection probe that includes the sequence:

TTCACTGATTCCGAGAGAACAGTGT-CACGGTTAAAGGATA-AGGAACTCTTCTGGAAT-GACTTTGCGGGCTGTTGACGA (SEQ ID NO: 6); and a detectable probe, such as the TaqMan® probe having the structure:

6FAM-AAGGAACTCTTCTGGAATGA-MGBNFQ (SEQ ID NO: 9). In particular embodiments, the kit further includes PCR primers, such as a forward PCR primer having the sequence: GAGAACAGTGTCACGGTTAAAGGA (SEQ ID NO: 10), and a reverse PCR primer having the sequence: CGTCAACAGCCCGCAAA (SEQ ID NO: 11).

DETAILED DESCRIPTION OF THE INVENTION

Figure 1:
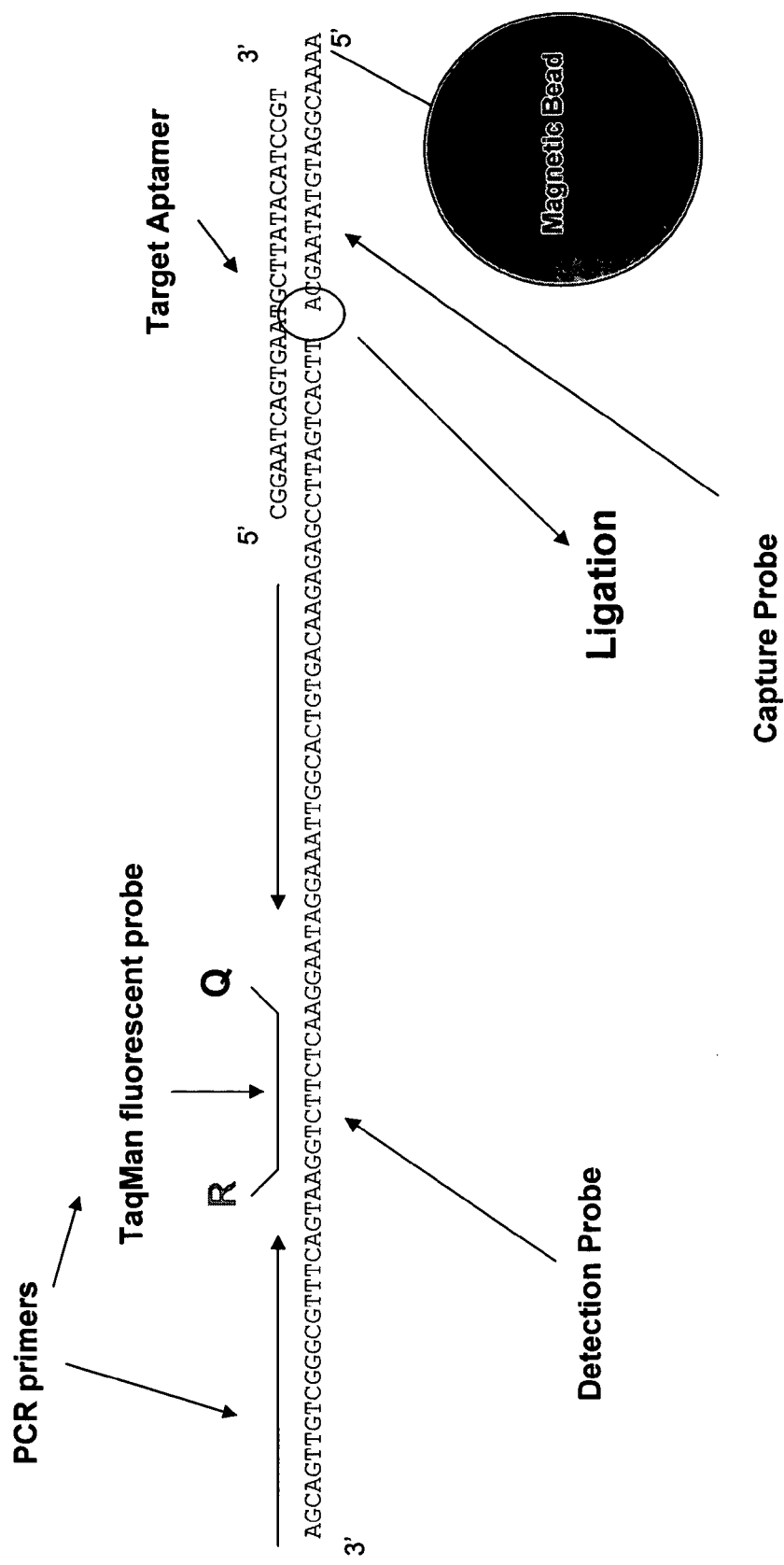
FIG. 1 is a diagrammatic representation of a dual hybridization assay format in which the target aptamer (a VEGF aptamer shown at top in the 5'-3' orientation; SEQ ID NO: 24) is bound by hybridization to a capture probe (shown in 3'-5' orientation; SEQ ID NO: 3), which itself is to attached to a magnetic bead. The capture probe is adjacent and capable of ligation to the detection probe (also shown in the 3'-5' orientation; SEQ ID NO: 6). The relative position of hybridization of the Real Time-PCR primers and fluorescent TaqMan® probe to the detection probe is also shown.
Figure 2:
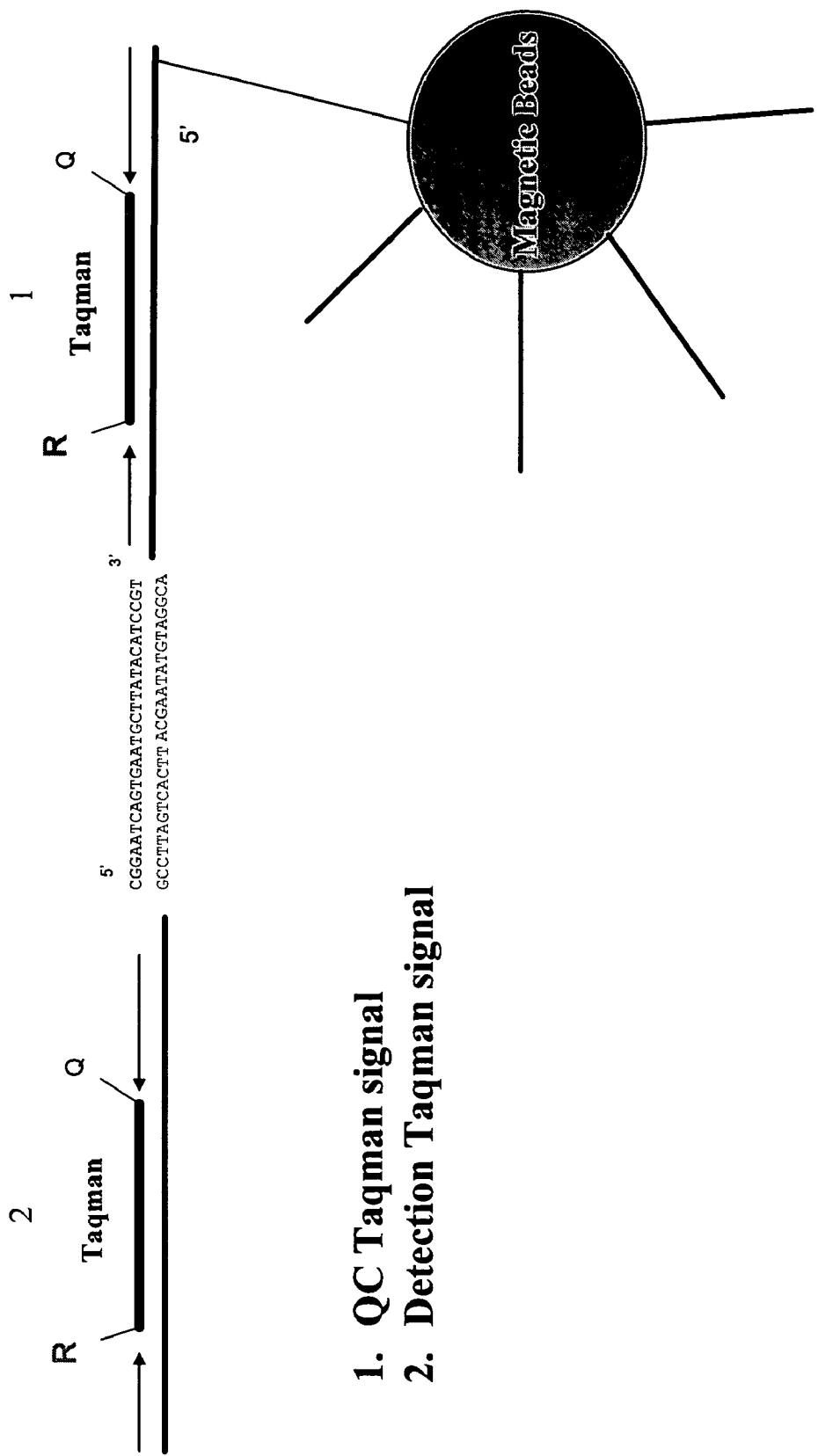
FIG. 2 is a diagrammatic representation of a quality control dual hybridization assay format in which the target aptamer (a VEGF aptamer shown at top in the 5'-3' orientation; SEQ ID NO: 24) is bound by hybridization to a quality control capture probe (shown in 3'-5' orientation, comprising the sequence SEQ ID NO: 2), which itself is to attached to a magnetic bead. The capture probe is adjacent and capable of ligation to the detection probe (also shown in the 3'-5' orientation, comprising the sequence SEQ ID NO: 5). The relative positions of hybridization of the Real Time-PCR primers and fluorescent TaqMan® probes to the detection probe and the quality control capture probe are also shown.

The patent and scientific literature referred to herein establishes knowledge that is available to those of skill in the art. The issued U.S. patents, allowed applications, published foreign applications, and references, that are cited herein are hereby incorporated by reference to the same extent as if each was specifically and individually indicated to be incorporated by reference.

General

In general, modified oligonucleotides such as aptamers, RNAi, siRNA, antisense oligonucleotides, and ribozymes are difficult to reliably detect and accurately quantify from a biological sample, in part because of their relatively short length and the presence of chemical modifications that, while enhancing activity and/or stability, can interfere with reliable detection and quantification. In particular, the reliable detection and accurate quantification of PEGylated oligonucleotides has not generally been achieved. Accordingly, the methods described herein are useful for reliably detecting and/or accurately quantifying oligonucleotides that are present in even minute quantities in a biological sample, including modified oligonucleotides that function as aptamers, RNAi, siRNA, antisense oligonucleotides or ribozymes.

Definitions

All technical and scientific terms used herein, unless otherwise defined below, are intended to have the same meaning as commonly understood by one of ordinary skill in the art; references to techniques employed herein are intended to refer to the techniques as commonly understood in the art, including variations on those techniques or substitutions of equivalent or later-developed techniques which would be apparent to one of skill in the art. In order to more clearly and concisely describe the subject matter which is the invention, the following definitions are provided for certain terms which are used in the specification and appended claims.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., *Diagnostic Molecular Microbiology: Principles and Applications*, D. H. Persing et al., Ed., American Society for Microbiology, Washington, D.C. (1993). The product of amplification is termed an amplicon. As used herein, "amplified DNA" or "amplicon" refers to the product of nucleic acid amplification of a target nucleic acid sequence that is part of a nucleic acid template. The amplicon is of a length and has a sequence that is diagnostic for the event. Alternatively, a primer pair can be derived from flanking sequence on both sides of the inserted DNA so as to produce an amplicon that includes the entire insert.

As used herein, the term "aptamer" means any polynucleotide, or salt thereof, having selective binding affinity for a non-polynucleotide molecule (such as a protein) via non-covalent physical interactions. An aptamer is a polynucleotide that binds to a ligand in a manner analogous to the binding of an antibody to its epitope. Aptamers of the invention include those comprising modified oligonucleotides, as described herein, including those having 5'-PEGylations, 2'-ribonucleotide substitutions, phosphate backbone modifications, and 5'-5' and 3'-3' inverted cap sequences, as well modification with a high molecular weight, soluble steric group.

By "biological sample" is intended any biological sample obtained from an individual, body fluid, cell line, tissue culture, or other source which contains a modified oligonucleotide. As indicated, biological samples include body fluids (such as vitreous humor, sera, plasma, urine, synovial fluid and spinal fluid). Methods for obtaining such biological samples using tissue biopsies and body fluids from mammals are well known in the art. The methods of the present invention may be used to detect and/or quantitate nucleic acids in any suitable biological sample. In one embodiment the methods of the present invention is used to detect and/or quantitate nucleic acids in eye tissues and fluids. Eye tissues and fluids include, but are not limited to, for example, those in, on or around the eye, such as the vitreous, conjunctiva, cornea, sclera, iris, crystalline lens, ciliary body, choroid, retina and optic nerve.

"Hybridization," as used herein refers to the association of two or more polynucleotides by complete or partial complementary base pairing.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

The term "oligomer," as used herein, refers to a polymer whose molecular weight is too low to be considered a polymer. Oligomers typically have molecular weights in the hundreds, but polymers typically have molecular weights in the thousands or higher.

The term "polyethylene glycol," or PEG refers to any polymer of general formula $H(OCH_2CH_2)_nOH$, wherein n is greater than 4. The average relative molecular mass of a polyethylene glycol is sometimes indicated by a suffixed number (e.g., polyethylene glycol 4000).

As used herein, "polymerase chain reaction," or "PCR," refers to a method whereby a specific sequence of nucleotides is amplified by polymerase priming from polynucleotides complementary to the specific sequence. The specific sequence targeted for amplification is replicated, typically by a thermostable Taq DNA polymerase, which primes off the complementary polynucleotides which are complementary to opposite strands of the two terminal regions of target nucleotide sequence to be amplified.

The terms "polynucleotide" and "oligonucleotide," as used herein, are any molecule that contains from about ten to about two hundred modified or unmodified nucleotide units connected by phosphodiester or modified phosphodiester linkages, such as phosphorodithioate or phorphorothioate linkages, between one position on the glycose moiety of one nucleotide unit (e.g., the 3' position) and another (e.g., the 5' position) on the glycose moiety of the adjacent one. The terms "polynucleotide" and "oligonucleotide" are meant to encompass any molecule comprising a sequence of covalently joined nucleosides or modified nucleosides which has selective binding affinity for a naturally-occurring nucleic acid of complementary or substantially complementary sequence under appropriate conditions (e.g., pH, temperature, solvent, ionic strength, electric field strength). Polynucleotides include naturally-occurring nucleic acids as well as nucleic acid analogues with modified nucleosides or internucleoside linkages, and molecules which have been modified with linkers or detectable labels which facilitate conjugation or detection. Polynucleotides further include extensively modified derivatives such as peptide nucleic acids (PNAs), which are still capable of specifically hybridizing to a complementary sequence. PNAs have a backbone that is composed of repeating N-(2-aminoethyl)-glycine units linked by peptide bonds, and the various purine and pyrimidine bases are linked to the backbone by methylene carbonyl bonds. As used herein, the term "polynucleotides" includes RNA or DNA (either double or single stranded (coding or antisense), or RNA/DNA hybrid sequences of more than one nucleotide in either single chain or duplex form (although each of the above species may be particularly specified). The term "nucleotide" as used in reference to a "polynucleotide" of the invention, is used as an adjective to describe molecules comprising RNA, DNA, or RNA/DNA hybrid sequences of any length in single-stranded or duplex form. The term "nucleotide" as used in reference to a "polynucleotide" of the invention, is also used herein as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. Although the term "nucleotide", again as used in reference to a "polynucleotide" of the invention, is also used herein to encompass "modified nucleotides" which comprise at least one modifications (a) an alternative linking group, (b) an analogous form of purine, (c) an analogous form of pyrimidine, or (d) an analogous sugar, for examples of analogous linking groups, purine, pyrimidines, and sugars see for example PCT publication No. WO 95/04064. Useful modifications of the present invention include, but are not limited to, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v) ybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl) uracil, and 2,6-diaminopurine. Methylenemethylimino linked oligonucleosides as well as mixed backbone compounds having, may be prepared as described in U.S. Pat. Nos. 5,378,825; 5,386,023; 5,489,677; 5,602,240; and 5,610,289. Formacetal and thioformacetal linked oligonucleosides may be prepared as described in U.S. Pat. Nos. 5,264,562 and 5,264,564. Ethylene oxide linked oligonucleosides may be prepared as described in U.S. Pat. No. 5,223,618. Phosphinate oligonucleotides may be prepared as described in U.S. Pat. No. 5,508,270. Alkyl phosphonate oligonucleotides may be prepared as described in U.S. Pat. No. 4,469,863. 3'-Deoxy-3'-methylene phosphonate oligonucleotides may be prepared as described in U.S. Pat. Nos. 5,610,289 or 5,625,050. Phosphoramidite oligonucleotides may be prepared as described in U.S. Pat. No. 5,256,775 or U.S. Pat. No. 5,366,878. Alkylphosphonothioate oligonucleotides may be prepared as described in published PCT applications WO 94/17093 and WO 94/02499. 3'-Deoxy-3'-amino phosphoramidate oligonucleotides may be prepared as described in U.S. Pat. No. 5,476,925. Phosphotriester oligonucleotides may be prepared as described in U.S. Pat. No. 5,023,243. Borano phosphate oligonucleotides may be prepared as described in U.S. Pat. Nos. 5,130,302 and 5,177,198. The polynucleotide sequences of the invention may be prepared by any known method, including synthetic, recombinant, ex vivo generation, or a combination thereof, as well as utilizing any purification methods known in the art.

As used herein, the term "nucleoside" means any of the naturally occurring ribonucleosides or deoxyribonucleosides: adenosine, cytosine, guanosine, thymosine or uracil.

The term "modified nucleotide" or "modified nucleoside" or "modified base" refer to variations of the standard bases, sugars and/or phosphate backbone chemical structures occurring in ribonucleic (i.e., A, C, G and U) and deoxyribonucleic (i.e., A, C, G and T) acids. For example, $G_m$ represents 2'-methoxyguanylic acid, $A_m$ represents 2'-methoxyadenylic acid, $C_f$ represents 2'-fluorocytidylic acid, $U_f$ represents 2'-fluorouridylic acid, $A_r$ represents riboadenylic acid. The aptamer includes cytosine or any cytosine-related base including 5-methylcytosine, 4-acetylcytosine, 3-methylcytosine, 5-hydroxymethyl cytosine, 2-thiocytosine, 5-halocytosine (e.g., 5-fluorocytosine, 5-bromocytosine, 5-chlorocytosine, and 5-iodocytosine), 5-propynyl cytosine, 6-azocytosine, 5-trifluoromethylcytosine, N4, N4-ethanocytosine, phenoxazine cytidine, phenothiazine cytidine, carbazole cytidine or pyridoindole cytidine. The aptamer further includes guanine or any guanine-related base including 6-methylguanine, 1-methylguanine, 2,2-dimethylguanine, 2-methylguanine, 7-methylguanine, 2-propylguanine, 6-propylguanine, 8-haloguanine (e.g., 8-fluoroguanine, 8-bromoguanine, 8-chloroguanine, and 8-iodoguanine), 8-aminoguanine, 8-sulfhydrylguanine, 8-thioalkylguanine, 8-hydroxylguanine, 7-methylguanine, 8-azaguanine, 7-deazaguanine or 3-deazaguanine. The aptamer further includes adenine or any adenine-related base including 6-methyladenine, N6-isopentenyladenine, N6-methyladenine, 1-methyladenine, 2-methyladenine, 2-methylthio-N6-isopentenyladenine, 8-haloadenine (e.g., 8-fluoroadenine, 8-bromoadenine, 8-chloroadenine, and 8-iodoadenine), 8-aminoadenine, 8-sulfhydryladenine, 8-thioalkyladenine, 8-hydroxyladenine, 7-methyladenine, 2-haloadenine (e.g., 2-fluoroadenine, 2-bromoadenine, 2-chloroadenine, and 2-iodoadenine), 2-aminoadenine, 8-azaadenine, 7-deazaadenine or 3-deazaadenine. Also included is uracil or any uracil-related base including 5-halouracil (e.g., 5-fluorouracil, 5-bromouracil, 5-chlorouracil, 5-iodouracil), 5-(carboxyhydroxylmethyl)uracil, 5-carboxymethylaminomethyl-2-thiouracil, 5-carboxymethylaminomethyluracil, dihydrouracil, 1-methylpseudouracil, 5-methoxyaminomethyl-2-thiouracil, 5'-methoxycarbonylmethyluracil, 5-methoxyuracil, 5-methyl-2-thiouracil, 2-thiouracil, 4-thiouracil, 5-methyluracil, uracil-5-oxyacetic acid methylester, uracil-5-oxyacetic acid, pseudouracil, 5-methyl-2-thiouracil, 2-thiouracil, 3-(3-amino-3-N-2-carboxypropyl) uracil, 5-methylaminomethyluracil, 5-propynyl uracil, 6-azouracil, or 4-thiouracil. Examples of other modified base variants known in the art include, without limitation, those listed at 37 C.F.R. §1.822(p) (1), e.g., 4-acetylcytidine, 5-(carboxyhydroxylmethyl)uridine, 2'-methoxycytidine, 5-carboxymethylaminomethyl-2-thioridine, 5-carboxymethylaminomethyluridine, dihydrouridine, 2'-O-methylpseudouridine, β-D-galactosylqueosine, inosine, N6-isopentenyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, β-D-mannosylqueosine, 5-methoxycarbonylmethyluridine, 5-methoxyuridine, 2-methylthio-N6-isopentenyladenosine, N-((9-β-D-ribofuranosyl-2-methylthiopurine-6-yl)carbamoyl)threonine, N-((9-β-D-ribofuranosylpurine-6-yl)N-methyl-carbamoyl) threonine, urdine-5-oxyacetic acid methylester, uridine-5-oxyacetic acid (v), wybutoxosine, pseudouridine, queosine, 2-thiocytidine, 5-methyl-2-thiouridine, 2-thiouridine, 4-thiouridine, 5-methyluridine, N-((9-β-D-ribofuranosylpurine-6-yl)carbamoyl)threonine, 2'-O-methyl-5-methyluridine, 2'-O-methyluridine, wybutosine, 3-(3-amino-3-carboxypropyl)uridine. Nucleotides also include any of the modified nucleobases described in U.S. Pat. Nos. 3,687,808, 3,687,808, 4,845,205, 5,130,302, 5,134,066, 5,175,273, 5,367,066, 5,432,272, 5,457,187, 5,459,255, 5,484,908, 5,502,177, 5,525,711, 5,552,540, 5,587,469, 5,594,121, 5,596,091, 5,614,617, 5,645,985, 5,830,653, 5,763,588, 6,005,096, and 5,681,941. Examples of modified nucleoside and nucleotide sugar backbone variants known in the art include, without limitation, those having, e.g., 2' ribosyl substituents such as F, SH, $SCH_3$, OCN, Cl, Br, CN, $CF_3$, $OCF_3$, $SOCH_3$, $SO_2CH_3$, $ONO_2$, $NO_2$, $N_3$, $NH_2$, $OCH_2CH_2OCH_3$, $O(CH_2)_2ON(CH_3)_2$, $OCH_2OCH_2N(CH_3)_2$, $O(C_{1-10}$ alkyl), $O(C_{2-10}$ alkenyl), $O(C_{2-10}$ alkynyl), $S(C_{1-10}$ alkyl), $S(C_{2-10}$ alkenyl), $S(C_{2-10}$ alkynyl), $NH(C_{1-10}$ alkyl), $NH(C_{2-10}$ alkenyl), $NH(C_{2-10}$ alkynyl), and O-alkyl-O-alkyl. Desirable 2' ribosyl substituents include 2'-methoxy(2'-$OCH_3$), 2'-aminopropoxy (2'$OCH_2CH_2CH_2NH_2$), 2'-allyl(2'-$CH_2$-CH=$CH_2$), 2'-O-allyl(2'-O-$CH_2$-CH=$CH_2$), 2'-amino(2'-$NH_2$), and 2'-fluoro (2'-F). The 2'-substituent may be in the arabino (up) position or ribo (down) position.

As used herein, the term "5'-5' inverted nucleotide cap" means a first nucleotide covalently linked to the 5' end of an oligonucleotide via a phosphodiester linkage between the 5' position of the first nucleotide and the 5' terminus of the oligonucleotide The term "3'-3' inverted nucleotide cap" is used herein to mean a last nucleotide covalently linked to the 3' end of an oligonucleotide via a phosphodiester linkage between the 3' position of the last nucleotide and the 3' terminus of the oligonucleotide.

The term "steric", as in "steric hindrance," refers to the restriction or prevention of the binding or interaction of one molecular entity (e.g., a protein) with another (e.g., an interacting protein). The term "steric hindrance" includes the effect of sterically enhanced aptamers having a soluble, high molecular weight steric group, in restricting or preventing the binding of an aptamer's target protein with the target protein's binding partner (e.g., a ligand with its receptor) due to the sizes and/or spatial disposition of atoms or groups in the steric group.

"Therapeutic" as used herein, includes treatment and/or prophylaxis. When used, therapeutic refers to humans as well as other animals.

"VEGF aptamers" or "Anti-VEGF aptamers" are meant to encompass polynucleotide aptamers that bind to, and inhibit the activity of, VEGF. Such anti-VEGF aptamers may be RNA aptamers, DNA aptamers or aptamers having a mixed (i.e., both RNA and DNA) composition. Such aptamers can be identified using known methods. For example, Systematic Evolution of Ligands by Exponential enrichment, or SELEX, methods can be used as described in U.S. Pat. Nos. 5,475,096 and 5,270,163, each of which are incorporated herein by reference in its entirety. Anti-VEGF aptamers include the sequences described in U.S. Pat. Nos. 6,168,778, 6,051,698, 5,859,228, and 6,426,335, each of which are incorporated herein by reference in its entirety. The sequences can be modified to include 5'-5' and/or 3'-3' inverted caps. (See Adamis, A. P. et al., published application No. WO 2005/014814, which is hereby incorporated by reference in its entirety).

Unless specifically indicated otherwise, the word "or" is used herein in the inclusive sense of "and/or" and not the exclusive sense of "either/or."

As used herein, the terms "increase" and "decrease" mean, respectively, a statistically significantly increase (i.e., $p<0.1$) and a statistically significantly decrease (i.e., $p<0.1$).

The recitation of a numerical range for a variable, as used herein, is intended to convey that the invention may be practiced with the variable equal to any of the values within that range. Thus, for a variable which is inherently discrete, the variable can be equal to any integer value within the numerical range, including the end-points of the range. Similarly, for a variable which is inherently continuous, the variable can be equal to any real value within the numerical range, including the end-points of the range. As an example, and without limitation, a variable which is described as having values between 0 and 2, can be 0, 1 or 2 for variables which are inherently discrete, and can be 0.0, 0.1, 0.01, 0.001, or any other real value $\geq 0$ and $\leq 2$ for variables which are inherently continuous.

Modified Oligonucleotide Targets

The modified oligonucleotides that can be detected and/or quantified using the methods described herein include modified RNA, modified DNA, aptamer, antisense, ribozyme, RNAi and siRNA molecules. Such molecules can contain synthetic nucleic acid analogs or a combination of naturally occurring and synthetic nucleic acid analogs. Synthetic nucleic acid analogs include those containing one or more backbone, base, or sugar modifications. Such modifications are known in the art, for example, see Verma et. al. ((1988) *Ann. Rev. Biochem.* 67:99-134). In particular, modified nucleic acid molecules that can be sequenced using the methods include nucleic acid molecules containing modifications such as fluorination, methylation, pegylation (e.g., at the 5' terminus), an inverted deoxythymidine cap, or other modifications of the 5' or 3' ends. The modified molecules can contain one of more modifications. For example, the molecule can contain fluorine and methyl groups.

The modified oligonucleotides to be analyzed by the method of the invention may include one or more modified internucleoside linkages. Such modified internucleoside linkages include phosphorothioate and/or phosphorodithioate linkages. The number of phosphorothioate and/or phosphorodithioate internucleotide linkages can range from 1 to as many internucleotide linkages as are present in the oligonucleotide. For example, modified oligonucleotides according to the invention may range from about 10 to about 100 nucleotides in length, and most usefully from about 20 to about 50 nucleotides in length. Thus, in latter embodiment, oligonucleotides according to the invention will have from 19 to about 49 phosphorothioate and/or phosphorodithioate internucleotide linkages.

The modified oligonucleotides to be analyzed by the method of the invention may include those having one or 2'-substituted ribonucleotides or combinations thereof. For purposes of the invention, the term "2'-substituted" means substitution of the 2'-OH of the ribose molecule with, e.g. 2'-OMe, 2'-O-allyl, 2'-O-aryl, 2'-O-alkyl, 2'-halo (e.g., fluro, chloro, bromo or iodo), or 2'-amino, but not with 2'-H, wherein allyl, aryl, or alkyl groups may be unsubstituted or substituted, e.g., with halo, hydroxy, trifluoromethyl, cyano, nitro, acyl, acyloxy, alkoxy, carboxyl, carbalkoxyl or amino groups. Modified oligonucleotides according to the invention may contain one or more ribonucleotides or 2'-substituted ribonucleotides. For example, such oligonucleotides may have 6 or more ribonucleotides and/or 2'-substituted ribonucleotides to enhance duplex stability. Such ribonucleotides and/or 2'-substituted ribonucleotides can be present singly, in pairs, or in larger contiguous segments, and may be present at any position within the oligonucleotide or at multiple positions within the oligonucleotide. Such ribonucleotides and/or 2'-substituted ribonucleotides may comprise as many as all but one nucleoside within the oligonucleotides. Thus, in a particularly useful embodiment, having from about 20 to about 50 nucleotides, the number of ribonucleosides or 2'-substituted ribonucleotides will range from about 20 to about 50. The modified oligonucleotides may further include deoxyribonucleotide residues.

The modified oligonucleotides (e.g., aptamers) for use in the method of the invention particularly includes those modified by a soluble, high molecular weight steric groups that may be conjugated to the oligonucleotide (e.g., target-specific aptamer) at any position on the nucleic acid sequence (see, U.S. application Ser. No. 11/105,279).

For example, conjugation of the steric group may be through the 5' end of the aptamer nucleic acid, the 3' end of the aptamer nucleic acid, or any position along the aptamer nucleic acid sequence between the 5' and 3' ends. For example, the high molecular weight steric group may be conjugated to the aptamer at an exocyclic amino group on a base, a 5-position of a pyrimidine nucleotide, a 8-position of a purine nucleotide, a hydroxyl group of a phosphate, or a hydroxyl group of a ribose group of the aptamer nucleic acid sequence. Means for chemically linking high molecular weight steric groups to aptamer nucleic acid sequences at these various positions are known in the art and/or exemplified below.

Such high molecular weight steric groups generally include any soluble high molecular weight compound that has a sufficient hydrodynamic volume to sterically interfere with the interaction between the aptamer-bound target and its binding partner. Examples include polymers (e.g., polyethylege glycol), gel-forming compounds and the like. The optimal characteristics of a particular soluble high molecular weight steric group may be optimized using the procedures taught herein and the methods and compositions taught herein. Examples of particularly useful steric groups of the invention include polysaccharides, such as glycosaminoglycans, hyaluronans, and alginates, polyesters, high molecular weight polyoxyalkylene ether (such as Pluronic™), polyamides, polyurethanes, polysiloxanes, polyacrylates, polyols, polyvinylpyrrolidones, polyvinyl alcohols, polyanhydrides, carboxymethyl celluloses, other cellulose derivatives, Chitosan, polyadlehydes or polyethers. Particularly useful steric groups will have a molecular weight of from about a molecular weight of about 20 to about 100 kDa, and/or a hydrodynamic volume of sufficient size to provide steric hindrance (e.g., to block binding of the antagonist aptamer target with a target binding partner, such as a ligand with its receptor).

Furthermore, the addition of non-immunogenic, high molecular weight or lipophilic compounds to the 5' end, to improve nuclease resistance and/or other pharmacokinetic properties, has also been described (see, e.g., U.S. Pat. Nos. 6,011,020, 6,147,024, 6,229,002, 6,426,335, 6,465,188, and 6,582,918). Examples of lipophilic groups are saturated or unsaturated hydrocarbons such as alkyl, alkenyl or other lipid groups. Sterols (e.g., cholesterol) and other pharmaceutically acceptable adjuvants (including anti-oxidants like alpha-tocopherol) may also be included to improve vesicle stability or confer other desirable characteristics. In general, such "lipophilic compounds" for conjugation to form a modified oligonucleotide, are compounds which have the propensity to associate with or partition into lipid and/or other materials or phases with low dielectric constants, including structures that are comprised substantially of lipophilic components. Lipophilic compounds include lipids as well as non-lipid containing compounds that have the propensity to associate with lipid (and/or other materials or phases with low dielectric constants). Cholesterol, phospholipids, and glycerolipids, such as dialkylglycerol, and diacylglycerol, and glycerol amide lipids are further examples of such lipophilic compounds.

The modified oligonucleotides useful in the method of the invention particularly include aptamers. Aptamers are nucleic acid molecules having a tertiary structure that permits them to specifically bind to protein ligands (e.g., Osborne, et al., 1997, *Curr. Opin. Chem. Biol.* 1:5-9; and Patel, 1997, *Curr. Opin. Chem. Biol.* 1:32-46). Such molecules can be selected from libraries of nucleic acids containing modified bases (e.g., using Systematic Evolution of Ligands by Exponential enrichment (SELEX)). The SELEX process: a surprising source of therapeutic and diagnostic compounds. *Gold L. Harvey Lect.* 1995-96;91:47-57. In some cases, a selected nucleic acid such as an aptamer is, subsequent to selection, chemically modified (for example, by methylation) and/or conjugated to, e.g., a polyethylene glycol, lipid, lipoprotein, or liposome. Although the sequence of the original SELEX-selected nucleic acid may be known, it can be desirable to confirm the nucleic acid sequence in subsequent applications. For example, it may be desirable or even required that the nucleic acid sequence of the molecule be confirmed in a manufacturing protocol or for a drug approval process. However, there is substantial evidence and belief in the art that certain types of modifications preclude sequencing of modified nucleic acid molecules.

Aptamers nucleic acid sequences have been made that bind to a wide variety of target molecules. The aptamer nucleic acid sequences of the invention can be comprised entirely of RNA or partially of RNA, or entirely or partially of DNA and/or other nucleotide analogs. Aptamers are typically developed to bind particular ligands by employing known in vivo or in vitro (most typically, in vitro) selection techniques known as SELEX. Methods of making aptamers are described, for example, in Ellington and Szostak (1990) Nature 346:818; Tuerk and Gold (1990) Science 249:505; U.S. Pat. Nos. 5,582,981; 5,756,291 and 5,270,163; PCT Publication Nos. WO 99/54506, WO 99/27133, WO 97/42317, and WO 00/20040; Lorsch and Szostak (1994) Biochem. 33:973; Mannironi et al., (1997) Biochem. 36:9726; Blind (1999) Proc. Nat'l. Acad. Sci. USA 96:3606-3610; and Huizenga and Szostak (1995) Biochem. 34:656-665.

Generally, in their most basic form, in vitro selection techniques for identifying RNA aptamers involve first preparing a large pool of DNA molecules of the desired length that contain at least some region that is randomized or mutagenized. For instance, a common oligonucleotide pool for aptamer selection might contain a region of 20-100 randomized nucleotides flanked on both ends by an about 10-30 nucleotide long region of defined sequence useful for the binding of PCR primers. The oligonucleotide pool is amplified using standard PCR techniques. The DNA pool is then transcribed in vitro. The RNA transcripts are then subjected to affinity chromatography. The transcripts are most typically passed through a column or contacted with magnetic beads or the like on which the target ligand has been immobilized. RNA molecules in the pool which bind to the ligand are retained on the column or bead, while nonbinding sequences are washed away. The RNA molecules which bind the ligand are then reverse transcribed and amplified again by PCR (usually after elution). The selected pool sequences are then put through another round of the same type of selection. Typically, the pool sequences are put through a total of about three to ten iterative rounds of the selection procedure. The cDNA is then amplified, cloned, and sequenced using standard procedures to identify the sequence of the RNA molecules which are capable of acting as aptamers for the target ligand.

The association constant for the aptamer and associated ligand is, for example, such that the ligand functions to bind to the aptamer and have the desired effect at the concentration of ligand obtained upon administration of the ligand. For in vivo use, for example, the association constant should be such that binding occurs below the concentration of ligand that can be achieved in the serum or other tissue (such as ocular vitreous fluid). For example, the required ligand concentration for in vivo use is also below that which could have undesired effects on the organism.

The aptamer nucleic acid sequences, in addition to including RNA, DNA and mixed compositions, may be modified. For example, certain modified nucleotides can confer improved characteristic on high-affinity nucleic acid ligands containing them, such as improved in vivo stability or improved delivery characteristics. Examples of such modifications include chemical substitutions at the ribose and/or phosphate and/or base positions. SELEX-identified nucleic acid ligands containing modified nucleotides are described in U.S. Pat. No. 5,660,985, entitled "High Affinity Nucleic Acid Ligands Containing Modified Nucleotides," that describes oligonucleotides containing nucleotide derivatives chemically modified at the 5- and 2'-positions of pyrimidines. U.S. Pat. No. 5,637,459, supra, describes highly specific nucleic acid ligands containing one or more nucleotides modified with 2'-amino (2'-NH2), 2'-fluoro (2'-F), and/or 2'-O-methyl (2'-OMe). U.S. application Ser. No. 08/264,029, filed Jun. 22, 1994, entitled "Novel Method of Preparation of Known and Novel 2' Modified Nucleosides by Intramolecular Nucleophilic Displacement," describes oligonucleotides containing various 2'-modified pyrimidines.

The aptamer nucleic acid sequences that can be analyzed by the method of the invention further may be combined with other selected oligonucleotides and/or non-oligonucleotide functional units as described in U.S. Pat. No. 5,637,459, entitled "Systematic Evolution of Ligands by Exponential Enrichment: Chimeric SELEX," and U.S. Pat. No. 5,683,867, entitled "Systematic Evolution of Ligands by Exponential Enrichment: Blended SELEX," respectively.

The aptamer modified oligoncucleotides that can be analyzed by the method of the invention are designed to bind specifically to a biological target to achieve a particular therapeutic or diagnostic end. For example, aptamer antagonists of VEGF are useful in the treatment of diseases involving neovascularization. VEGF antagonists have been used to treat, for example, neovascular age-related macular degeneration (AMD), a progressive condition characterized by the presence of choroidal neovascularization (CNV) that results in more severe vision loss than any other disease in the elderly population (see Csaky et al. (2003) Ophthalmol. 110: 880-1). The SELEX process for obtaining target-specific aptamers in general, and VEGF aptamers and formulations in particular, are described in, e.g., U.S. Pat. Nos. 5,270,163, 5,475,096, 5,696,249, 5,670,637, 5,811,533, 5,817,785, 5,958,691, 6,011,020, 6,051,698, 6,147,204, 6,168,778, and 6,426,335.

Many other aptamer sequences have been developed that target various other biological targets. For example aptamer sequences have been developed that target PDGF (see U.S. Pat. Nos. 5,668,264, 5,674,685, 5,723,594, 6,229,002, 6,582,918, and 6,699,843), basic FGF (see U.S. Pat. Nos. 5,459,015, and 5,639,868), CD40 (see U.S. Pat. No. 6,171,795), TGFb (see U.S. Pat. Nos. 6,124,449, 6,346,611, and 6,713,616), CD4 (see U.S. Pat. No. 5,869,641), chorionic gonadotropin hormone (see U.S. Pat. Nos. 5,837,456, and 5,849,890), HKGF (see U.S. Pat. Nos. 5,731,424, 5,731,144, 5,837,834, and 5,846,713), ICP4 (see U.S. Pat. No. 5,795,721), HIV-reverse transcriptase (see U.S. Pat. No. 5,786,462), HIV-integrase (see U.S. Pat. Nos. 5,587,468, and 5,756,287), HIV-gag (see U.S. Pat. Nos. 5,726,017), HIV-tat (see U.S. Pat. No. 5,637,461), HIV-RT and HIV-rev (see U.S. Pat. Nos. 5,496,938, and 5,503,978), HIV nucleocapsid (see U.S. Pat. Nos. 5,635,615, and 5,654,151), neutophil elastase (see U.S. Pat. Nos. 5,472,841, and 5,734,034), IgE (see U.S. Pat. Nos. 5,629,155, and 5,686,592), tachykinin substance P (see U.S. Pat. Nos. 5,637,682, and 5,648,214), secretory phospholipase A2 (see U.S. Pat. No. 5,622,828), thrombin (see U.S. Pat. No. 5,476,766), intestinal phosphatase (see U.S. Pat. Nos. 6,280,943, 6,387,635, and 6,673,553), tenascin-C (see U.S. Pat. Nos. 6,232,071, and 6,596,491), as well as to cytokines (see U.S. Pat. No. 6,028,186), seven transmembrane G protein-coupled receptors (see U.S. Pat. No. 6,682,886), DNA polymerases (see U.S. Patent. Nos. 5,693,502, 5,763,173, 5,874,557, and 6,020,130,) complement system proteins (see U.S. Pat. Nos. 6,395,888, and 6,566,343), lectins (see U.S. Pat. Nos. 5,780,228, 6,001,988, 6,280,932, and 6,544,959), integrins (see U.S. Pat. No. 6,331,394), hepatocyte growth factor/scatter factor (HGF/SP) or its receptor (c-met) (see U.S. Pat. No. 6,344,321), and angiopoietins (see WO 2002/026932). Still many more aptamers that target a desired biological target are possible given the adaptability of the SELEX-based methodology.

Particularly useful aptamer targets of the invention include adhesion molecules and their ligands, many of which have large, multidomain extracellular regions that facilitate cell communications and which are particularly amenable to the methods and compositions of the invention. Adhesion molecules include: the selectins (e.g., L-selectin (CD62L, which binds to sulfated GlyCAM-1, CD34, and MAdCAM-1)), E-selectin (CD62E) and P-selectin (CD62P)); the integrins (e.g., LFA-1 (CD11a), which bind to the ICAMs ICAM-1, ICAM-2 and ICAM-3, and CD11b which binds to ICAM-1, Factor X, iC3b and fibrinogen); the immunoglobulin (Ig) superfamily of proteins including the neural specific IgCAMS such as MAG (myelin-associated glycoprotein), MOG (myelin-oligodendrocyte glycoprotein), and NCAM-1 (CD56) and the systemic IgCAMs such as ICAM-1 (CD54) (which binds to LFA-1, see above), ICAM-2 (CD102), ICAM-3 (CD50), and CD44 (which binds to hyaluronin, anykyrin, fibronectin, MIP1b and osteopontin); as well as the cadherins (such as Cadherins E (1), N (2), BR (12), P (3), R (4), etc. and the Desmocollins, such as Desmocollin 1).

In some cases the modified oligonucleotide for detection is an antisense nucleic acid. An "antisense" nucleic acid can include a nucleotide sequence that is complementary to a "sense" nucleic acid encoding a protein, e.g., complementary to the coding strand of a double-stranded cDNA molecule or complementary to an mRNA sequence or can be complementary to a transcribed non-coding sequence (e.g., the 5' and 3' untranslated regions of a gene). The antisense nucleic acid can be complementary to an entire coding strand, or to only a portion thereof. Antisense molecules and other nucleic acid molecules can be chemically synthesized using naturally occurring nucleotides or variously modified nucleotides designed to increase the biological stability of the molecules or to increase the physical stability of the duplex formed between e.g., the antisense and sense nucleic acids, e.g., phosphorothioate derivatives and acridine substituted nucleotides can be used. The methods described herein can be used to detect and/or quantify such modified molecules. In one embodiment the antisense nucleic acid has the sequence (5' to 3'): CAC CCA AGA CAG CAG AAA G (SEQ ID NO: 17).

Nucleic acids containing other types of modifications can also be sequenced as described herein. For example, for systemic administration, nucleic acid molecules are modified such that they specifically bind to receptors or antigens expressed on a selected cell surface, e.g., by linking the nucleic acid molecule to a peptide or antibody that binds to cell surface receptors or antigens. Additional examples of modified nucleic acid molecules include those containing one or more 2'-o-methylribonucleotides (Inoue et al., 1987, *Nucleic Acids Res.* 15:6131-6148) or a chimeric RNA-DNA analogs (Inoue et al., 1987, *FEBS Lett.* 215:327-330). Nucleic acid molecules containing detectable labels (e.g., fluorescent, chemiluminescent, radioactive, or colorimetric) can be sequenced using the described methods.

A nucleic acid molecule can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup et al., 1996, *Bioorganic & Medicinal Chemistry* 4:5-23). As used herein, the terms "peptide nucleic acid" or "PNA" refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength (Hyrup et al., 1996, supra; Perry-O'Keefe et al. 1996, *Proc. Natl. Acad. Sci. USA* 93: 14670-14675).

In some cases, the modified nucleic acid includes appended groups such as peptides (e.g., for targeting host cell receptors in vivo), or agents facilitating transport across the cell membrane (see, e.g., Letsinger et al., 1989, *Proc. Natl. Acad. Sci. USA* 86:6553-6556; Lemaitre et al., 1987, *Proc. Natl. Acad. Sci. USA* 84:648-652; PCT Publication No. W088/09810), or the blood-brain barrier (see, e.g., PCT Publication No. W089/10134). In addition, oligonucleotides can be modified with hybridization-triggered cleavage agents (see, e.g., Krol et al., 1988, *Bio-Techniques* 6:958-976) or intercalating agents. (see, e.g., Zon, 1988, *Pharm. Res.* 5:539-549). To this end, the oligonucleotide can be conjugated to another molecule, (e.g., a peptide, hybridization triggered cross-linking agent, transport agent, or hybridization-triggered cleavage agent). Yet another type of modified nucleic acid that can be sequenced using the methods described herein are molecular beacon oligonucleotide primer and probe molecules having at least one region that is complementary to a selected nucleic acid, two complementary regions one having a fluorophore and one a quencher such that the molecular beacon is useful for quantitating the presence of the selected nucleic acid in a sample. Molecular beacon nucleic acids are described, for example, in U.S. Pat. Nos. 5,854,033; 5,866,336, and 5,876,930.

In some cases the modified oligonucleotide for detection is nucleic acid used for RNA interference (RNAi); a technique for gene silencing. An "RNAi" nucleic acid can include small fragments of double-stranded RNA (dsRNA) whose sequence matches a given gene interferes with the expression of that gene. The RNAi nucleic acid can be introduced into the cell to disrupt messenger RNA and prevent it from being translated into a protein. In one embodiment the RNAi nucleic acid has the sequence 5' to 3' UUG CAC AUU GCU CAG UUC AUA CAC C (SEQ ID NO: 18). The sequence is supplied with the following RNAi antisense strand (5' to 3'): GGU GUA UGA ACU GAG CAA UGU GCA A (SEQ ID NO: 19).

Polynucleotides

The polynucleotides for use in the dual hybridization detection/quantification methods of the invention include the first, i.e., capture probe, and second, i.e., detection probe, polynucleotides. The first and second polynucleotides generally each hybridize to a (non-overlapping) portion of the target modified oligonucleotide (e.g., aptamer). The polynucleotide nucleic acids of the invention can be DNA or RNA, or a mixture or synthetic, chemically modified, version thereof. The region of hybridization to the target of each of the first and second polynucleotides may correspond to either a 5' region or a 3' region of the target oligonucleotide, so long as the two targets are overlapping and, usefully, abutting so that they may be simultaneously fully hybridized to the target and, subsequently, optionally ligated together into a first polynucleotide-second polynucleotide conjugate.

By a polynucleotide which hybridizes to a "portion" of a polynucleotide is intended a polynucleotide (either DNA or RNA) hybridizing to at least about 8 nucleotides (nt), e.g., at least about 7, 8, 9, 10, 11, 12, 13, 15, 20, or about 30 or more nucleotides (e.g., 40, 50, or 60) nucleotides. In general the first and second polynucleotides of the invention hybridize to about any integer in the range of 10-30, 12-20 or 13-15 nucleotides, or, in sum, the entire length of the reference polynucleotide. These have uses, which include, but are not limited to, diagnostic probes and primers as discussed above and in more detail below. By a portion of a polynucleotide of "at least about 10 nt in length," for example, is intended to include the particularly recited ranges.

As used herein, the term "specifically hybridizes" or "specifically detects" refers to the ability of a nucleic acid molecule of the invention to hybridize to at least approximately 6, 8, 10, 11, 12, 13, 14, 15, 16, 17, 18, 19, 20, 21, 22, 23, 24, 25, 26, 27, 28, 29, 30, 32, 35, 40, 50, 100, or consecutive nucleotides of a target oligonucleotide, such as an aptamer (e.g. a VEGF aptamer), or a sequence complementary thereto, or naturally occurring mutants thereof.

Particularly useful polynucleotides hybridize specifically to a modified oligonucleotide of the invention. Specific polynucleotides of the present invention hybridize under appropriate stringency to a target oligonucleotide, such as a modified oligonucleotide (e.g., an aptamer). Appropriate stringency conditions which promote DNA hybridization, for example, are provided below in the examples (e.g., 6×SSC/ 1.0% sarkosyl). Other conditions which promote DNA hybridization include: 6.0× sodium chloride/sodium citrate (SSC) at about 25-45° C., followed by a wash of 2.0×SSC at 25-50° C. Other conditions are known to those skilled in the art or can be found in *Current Protocols in Molecular Biology*, John Wiley & Sons, N.Y. (1989), 6.3.1-6.3.6. In addition, the temperature in the wash step can be increased from low stringency conditions at room temperature, about 22° C., to higher stringency conditions at higher temperatures. Both temperature and salt may be varied, or either the temperature or the salt concentration may be held constant while the other variable is changed. In one useful embodiment, a target modified oligonucleotide will bind to one of the first or second polynucleotides (i.e., the capture and detection probes) under moderately stringent conditions, for example at about 2.0× SSC and about 40° C.

Useful polynucleotides have a sequence at least 75% homologous, at least 80%, at least 85%, at least 90% or at least 95% homologous with a target modified oligonucleotide sequence. For example, first and second polynucleotides having a sequence that differs from the nucleotide sequences shown in FIG. 1, and more generally, that have a sequence non-identical to the target modified oligonucleotide, are included in the invention.

Tags

The invention includes one or more tags for attachment to a polynucleotide of the invention. Particularly useful tags of the invention are attached to the capture probe (i.e., first polynucleotide) of the invention and allow for the immobilization of the capture probe and anything that has specifically hybridized to it (e.g., the target oligonucleotide or the target oligonucleotide and the detection probe (i.e., second polynucleotide)). The tag of the invention is useful in separating oligonucleotides and/or polynucleotides specifically associated with the capture probe, such as by washing or other means of separation known in the art (e.g., magnetic bead-mediated separation).

Examples of tags of the invention, for use, e.g., as joined to the first polynucleotide/capture probe of the invention, includes any immobilizing agent which may be used to join the tag-containing complex to a solid support (e.g., one which will resist removal by "washing"). Numerous solid supports, suitable as immobilizing moieties according to the invention, are well known in the art and widely described in the literature and generally speaking, the solid support may be any of the well-known supports or matrices which are currently widely used or proposed for immobilization, separation etc. in chemical or biochemical procedures. Thus, for example, the immobilizing moieties may take the form of particles, sheets, gels, filters, membranes, microfibre strips, tubes or plates, fibres or capillaries, made for example of a polymeric material e.g. agarose, cellulose, alginate, teflon, latex or polystyrene. Biochips may be used as solid supports to provide miniature experimental systems as described for example in Nilsson et al. ((1995) *Anal. Biochem.* 224: 400-408) or as a diagnostic tool. Particulate materials, especially beads, are generally useful for this purpose. For example, Sepharose or polystyrene beads may be used. The immobilizing moiety may comprise magnetic particles, which permit the ready separation of immobilized material by magnetic aggregation (e.g., streptavidin magnetic particles (Roche, cat. no. 1 641 778), which may be used with, e.g., a biotinylated capture probe. The requirement of such a moiety is that it is stable to the conditions of the wash. The magnetic beads can comprise optimal rare-earth neodymium permanent magnets. In one embodiment the magnetic beads are Dynabeads®. Dynabeads are uniform, monosized superparamagnetic beads composed of highly cross-linked polystyrene with magnetic material precipitated in pores evenly distributed throughout the particles. The particles are further coated with a hydrophilic layer of glycidyl ether, concealing the iron oxide inside the Dynabeads. Functional groups such as epoxides or carboxylic acids are then introduced on the surface. In particular embodiments, the invention uses Dynabeads® M-270 carboxylic acid (carboxylic acid coated) or Dynabeads® M-270 epoxy (epoxide coated).

The immobilizing support may carry further moieties for attachment of the polynucleotide. Generally speaking, these will comprise one of a pair of affinity binding partners, such as biotin and avidin or streptavidin, PNA (or DNA) and DNA binding protein (e.g. either the lac I repressor protein or the lac operator sequence to which it binds), antibodies (which may be mono- or polyclonal), antibody fragments or the epitopes or haptens of antibodies. In these cases, one partner of the binding pair is attached to (or is inherently part of) the immobilizing moiety and the other partner is attached to (or is inherently part of) the first polynucleotide (e.g., capture probe). The afore-mentioned binding moieties may be attached to the immobilizing support by methods well known in the art, which include for example, attachment-through hydroxyl, carboxyl, aldehyde or amino groups which may be provided by treating the immobilizing support to provide suitable surface coatings. For example, U.S. Pat. No. 4,654, 267 describes the introduction of many such surface coatings. Another exemplary tag and immobilizing support system is that described below, using a capture probe that contains a 5'-$NH_2$ group and magnetic beads that contain an epoxide or carboxylic acid group. Addition of the capture probe with the epoxide or carboxylic acid containing magnetic beads results in a magnetic bead-oligonucleotide complex.

Detectable Labels

In certain embodiments, the invention includes a detectable label, which may be attached to one of the polynucleotides of the invention (e.g., the "detection probe" or "second polynucleotide"). In one useful embodiment, the detectable label is a digoxigenin label.

Examples of detectable labels which may be employed include radio-labels, enzymes, fluorescent compounds, streptavidin, avidin, biotin, magnetic moieties, metal binding moieties, antigen (e.g., digoxigenin), haptens, or antibody moieties, and the like. Exemplary haptens include digoxigenin, DNP, and fluorescein (Holtke et al. (1992) *Biotechniques* 12(1): 104-113 and Olesen et al. (1993) *Biotechniques* 15(3): 480-485).

Detectable markers of the invention include, but are not limited to, radioactive labels, as well as colorimetric, luminescent, or fluorescent markers, or gold. Suitable radioactive labels include, but are not limited to: $^3$H, $^{14}$C, $^{32}$P, $^{33}$P; $^{35}$S, $^{36}$Cl, $^{51}$Cr, $^{57}$Co, $^{59}$Co, $^{59}$Fe, $^{90}$Y, $^{125}$I, $^{131}$I, and $^{186}$Re. Fluorescent markers include but are not limited to: fluorescein, rhodamine and auramine. Colorimetric markers include, but are not limited to: biotin, and digoxigenin. Methods of producing the polyclonal or monoclonal antibody are known to those of ordinary skill in the art. Further, the antibody or nucleic acid molecule complex may be detected by a second antibody which may be linked to an enzyme, such as alkaline phosphatase or horseradish peroxidase. Other enzymes which may be employed are known to one of ordinary skill in the art.

Ligation

The invention includes kits and methods for ligating a first and a second polynucleotide together, thereby increasing the stability of the ternary complex between the first and second polynucleotides and the target oligonucleotide. This optional ligation step increases the specificity and sensitivity of the method of the invention. Ligation may be achieved chemically or by use of appropriate naturally occurring ligases or variants thereof. While ligation represents only an optional feature of the invention, compared to hybridization alone, specificity and sensitivity of detection is increased significantly if a ligation step is included.

Ligation can be achieved using any available using any known enzymatic or chemical method. For example, where the nucleotide ends are deoxyribonucleotide polynucleotides, T4 DNA ligase may be used, while, where the nucleotide ends are ribonucleotide polynucleotides, an RNA ligase may be used. Furthermore, thermostable ligases, such as Pfu, Taq, and TTH DNA ligase may be used at elevated temperatures (e.g., 65° C.-72° C.) to improve specificity and efficiency while decreasing the required incubation time.

It is emphasized that any ligase may be used in the claimed method. Useful ligases are those that form phosphodiester bonds at nicks in double-stranded DNA, including ligases that fail to ligate the free ends of single-stranded DNA at a significant rate. Thermostable ligases are useful in this regard. The particular details of use of any of the suitable ligases are known in the art. For example: T4 DNA ligase (Davis et al., *Advanced Bacterial Genetics-A Manual for Genetic Engineering* (Cold Spring Harbor Laboratory, Cold Spring Harbor, N.Y., 1980)), *E. coli* DNA ligase (Panasnko et al. (1978) *J. Biol. Chem.* 253: 4590-4592), AMPLIGASE® (Kalin et al. (1992) *Mutat. Res.* 283(2): 119-123; Winn-Deen et al. (1993) *Mol. Cell. Probes* (England) 7(3):179-186), Taq DNA ligase (Barany (199) *Proc. Natl. Acad. Sci. USA* 88: 189-193 (1991), Thermus thermophilus DNA ligase (Abbott Laboratories), Thermus scotoductus DNA ligase and Rhodothermus marinus DNA ligase (Thorbjarnardottir et al. (1995) *Gene* 151: 177-180). T4 DNA ligase is useful for ligations involving RNA target sequences due to its ability to ligate DNA ends involved in DNA:RNA hybrids (Hsuih et al., Quantitative detection of HCV RNA using novel ligation-dependent polymerase chain reaction, American Association for the Study of Liver Diseases (Chicago, Ill., Nov. 3-7, 1995)). T4 RNA ligase can also be used to ligate DNA ends of nucleic acid strands hybridized to an RNA strand. Alternatively, the ligating agent may be a chemical, such as cyanogen bromide or a carbodiimide (Sokolova et al. (1988) *FEBS Lett.* 232: 153-155).

The ligation serves to join the 5' end of the first oligonucleotide probe to the 3' end of the second oligonucleotide probe (capture probe and detection probe, respectively) to form a contiguous functional single-stranded oligonucleotide molecule (a ligated amplifiably sequence). The presence of the ligated amplifiable sequence may be detected directly, e.g., by digoxigenin label. The presence of the labeled second polynucleotide in the ternary complex with the capture and target oligonucleotides, indicates the presence of the target nucleic acid in the sample. Alternatively, the ligated amplification sequence serves as the template for any of various amplification systems, such as PCR or SDA. Any of the second polynucleotide probe that remain unligated after treatment is not amplified in subsequent steps in the method.

As an alternative to ligation by enzymatic means (i.e., using a ligase), the capture and detection probes can be joined by chemical means (e.g., using psoralen moieties and UV light to crosslink the strands.

Amplification Detection and/or Quantification

The invention includes methods for amplifying an amplifiable sequence, e.g., an amplifiable sequence present on a detection probe. Basic PCR technology applies to amplification of a nucleic acid sequence of interest. Methods and compositions for basic PCR technology are well known in the art (see, e.g., Kellogg (1990) *Anal. Biochem.* 189: 202-8; and Pang (1990) *Nature* 343: 85-89). Nucleic acid amplification can be accomplished by any of the various nucleic acid amplification methods known in the art, including the polymerase chain reaction (PCR). A variety of amplification methods are known in the art and are described, for example, in U.S. Pat. Nos. 4,683,195 and 4,683,202, and in *PCR Protocols: A Guide to Methods and Applications*, ed. Innis et al., Academic Press, San Diego, 1990. Any known method for nucleic acid amplification may be used in the practice of the present invention.

Similarly, any known method for detection of the PCR amplification product may be employed. For example, agarose gel electrophoresis and staining with ethidium bromide is a common well known method of detecting DNA amplicons. Another method is Genetic Bit Analysis (Nikiforov, et al. *Nucleic Acid Res.* 22:4167-4175, 1994). The detection oligonucleotide is immobilized in wells of a microtiter plate. Following thermal amplification of the region of interest (using one primer in the inserted sequence and one in the adjacent flanking genomic sequence), a single-stranded thermal amplification product can be hybridized to the immobilized oligonucleotide and serve as a template for a single base extension reaction using a DNA polymerase and labeled ddNTPs (dideoxynucleotides triphosphates) specific for the expected next base. Readout may be fluorescent or ELISA-based. A signal indicates presence of the amplicon sequence due to successful amplification, hybridization, and single base extension.

In particularly useful embodiments, the invention includes an RT-PCR reaction for the sensitive detection and/or quantification of the detection probe/target oligonucleotide. In reverse transcriptase PCR (RT-PCR) a reverse transcription step is added to the basic PCR protocol. This adapts basic PCR methodology for detection and quantitation of specific RNA nucleic acids, e.g ribonucleotide polynucleotides.

Figure 3:
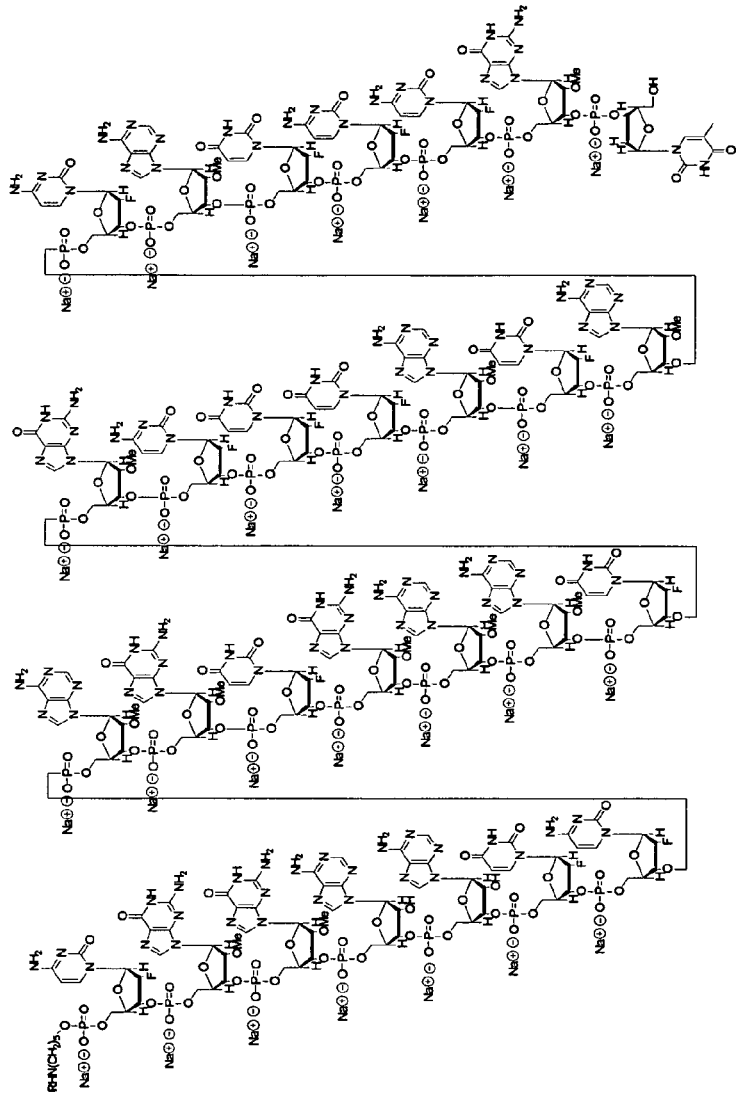
FIG. 3 is a schematic representation of the chemical structure of a PEGylated VEGF antagonist aptamer (i.e., Pegaptanib, Macugen® (EYE001)).
Figure 3:
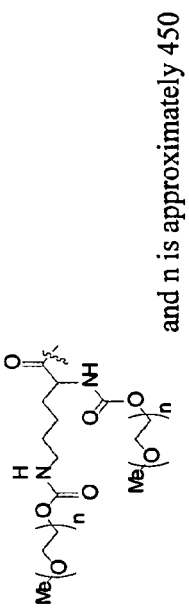

Methods for performing RT-PCR are known in the art. In brief, following synthesis of cDNA in a reverse transcription step, PCR is run to an appropriate end point in an amplification step, and then quantitation of reaction product can be carried out in a detection, i.e., assay, step. In a variation of RT-PCR known as "real time" PCR (or "kinetic PCR"), the amplification and detection steps are combined. The cycleby-cycle increase in the amount of PCR product is quantified in real time. This is accomplished by including a "probe" along with conventional forward and reverse primers in the amplification reaction. The probe, which hybridizes within the amplified sequence, typically is about 20-25 nucleotides in length. The commercially available TaqMan® probes (Applied Biosystems, Foster City, Calif.) include a fluorescent reporter moiety (dye) at the 5' terminus and a quencher moiety (dye) at the 3' terminus. In the intact probe, fluorescence of the reporter is strongly suppressed through internal quenching by a quencher moiety. As the exonuclease action of the advancing Taq polymerase digests the hybridized probe, the reporter is unquenched, resulting in fluorescence, which is detected and quantified (see FIG. 3).

Quantitation of polynucleotide by real-time PCR can be relative or absolute. In either case, quantitation of polynucleotide in a sample is by reference to an appropriate standard curve. In the case of standard curves for relative quantitation, quantity is expressed relative to a basis sample, which is often called the "calibrator." For the experimental samples, target quantity is determined from the standard curve and divided by the value of the calibrator. Thus, the calibrator becomes the 1× sample, and all other quantities are expressed as an n-fold difference relative to the calibrator. For example, in a study of the stability of an aptamer in a biological fluid, the untreated control aptamer not exposed to the biological sample can serve as a suitable calibrator. Because the experimental quantity is divided by the calibrator quantity, the standard curve unit, e.g., fluorescence intensity, drops out. This means that for relative quantitation, any source of modified oligonucleotide containing the target oligonucleotide can be used to create a standard curve, following preparation of a suitable dilution series. In contrast, absolute quantitation of oligonucleotide by real-time PCR requires a standard in which the absolute quantity of an RNA containing the target sequence is known independently. This can be obtained by simply generating a standard curve using a stock solution of the target modified oligonucleotide (e.g., aptamer). In one embodiment a pegaptanib standard curve is generated with concentration ranging from 1000 nM to 0.0016 nM. In further embodiments using other nucleic acids a standard curve is generated with concentration ranging from 100 nM to 0.008 nM in 1X Tissue (1:10 of the tissue stock to make 1X).

The development of novel chemistries and instrumentation platforms enabling detection of PCR products on a real-time basis has led to widespread adoption of real-time RT-PCR as the method of choice for quantitating nucleic acids.

At the start of a PCR reaction, reagents are in excess, template and product are at low enough concentrations that product renaturation does not compete with primer binding, and amplification proceeds at a constant, exponential rate. The point at which the reaction rate ceases to be exponential and enters a linear phase of amplification is extremely variable, even among replicate samples, but it appears to be primarily due to product renaturation competing with primer binding (since adding more reagents or enzyme has little effect). At some later cycle the amplification rate drops to near zero (plateaus), and little more product is made.

For the sake of accuracy and precision, it is necessary to collect quantitative data at a point in which every sample is in the exponential phase of amplification (since it is only in this phase that amplification is extremely reproducible). Analysis of reactions during exponential phase at a given cycle number should theoretically provide several orders of magnitude of dynamic range. Rare targets will probably be below the limit of detection, while abundant targets will be past the exponential phase. In practice, a dynamic range of 2-3 logs can be quantitated during end-point relative RT-PCR. In order to extend this range, replicate reactions may be performed for a greater or lesser number of cycles, so that all of the samples can be analyzed in the exponential phase.

Real-time PCR automates this otherwise laborious process by quantitating reaction products for each sample in every cycle. The result is a broad (e.g., about 107-fold) dynamic range, with no user intervention or replicates required. Data analysis, including standard curve generation and copy number calculation, is performed automatically. With increasing numbers of labs and core facilities acquiring the instrumentation required for real-time analysis, this technique is becoming the dominant RT-PCR-based quantitation technique.

Real-Time PCR Chemistries

Currently four different chemistries, TaqMan® (Applied Biosystems, Foster City, Calif., USA), Molecular Beacons, Scorpions® and SYBR® Green (Molecular Probes), are available for real-time PCR. All of these chemistries allow detection of PCR products via the generation of a fluorescent signal. TaqMan® probes, Molecular Beacons and Scorpions depend on Förster Resonance Energy Transfer (FRET) to generate the fluorescence signal via the coupling of a fluorogenic dye molecule and a quencher moeity to the same or different oligonucleotide substrates. SYBR Green is a fluorogenic dye that exhibits little fluorescence when in solution, but emits a strong fluorescent signal upon binding to double-stranded DNA.

TaqMan® Probes

Figure 4:
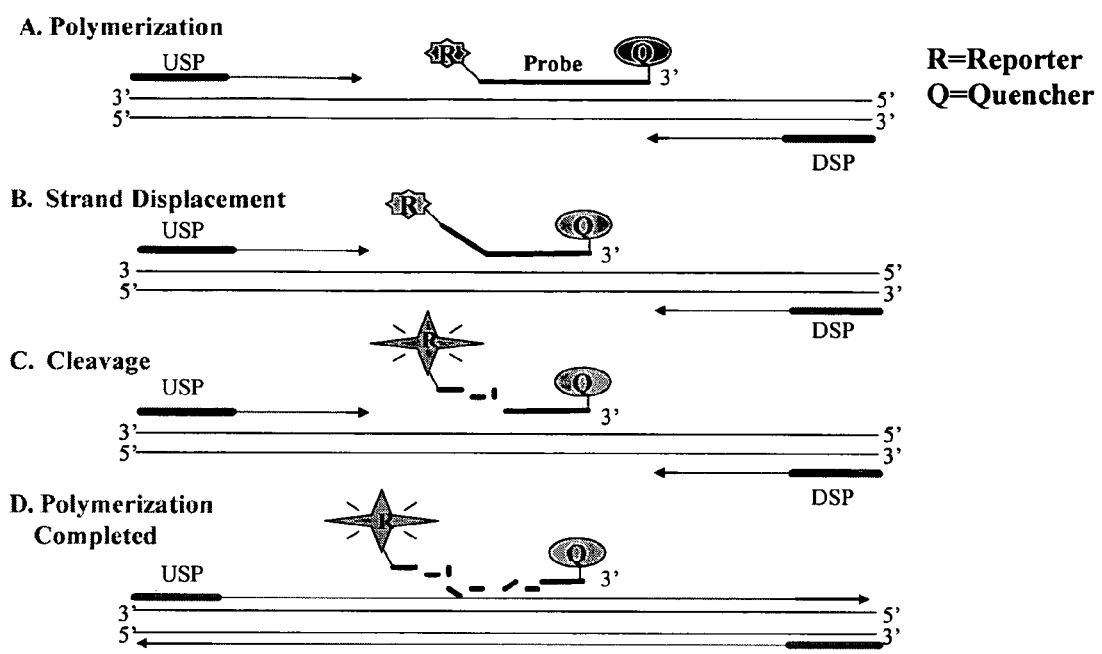
FIG. 4 is a diagrammatic representation of a REAL TIME-PCR reaction using TaqMan® fluorogenic 5' nuclease chemistry.

TaqMan® probes depend on the 5'-nuclease activity of the DNA polymerase used for PCR to hydrolyze an oligonucleotide that is hybridized to the target amplicon. TaqMan® probes are oligonucleotides that have a fluorescent reporter dye attached to the 5' end and a quencher moeity coupled to the 3' end. These probes are designed to hybridize to an internal region of a PCR product. In the unhybridized state, the proximity of the fluor and the quench molecules prevents the detection of fluorescent signal from the probe. During PCR, when the polymerase replicates a template on which a TaqMan® probe is bound, the 5'-nuclease activity of the polymerase cleaves the probe (see FIG. 4). This decouples the fluorescent and quenching dyes and FRET no longer occurs. Thus, fluorescence increases in each cycle, proportional to the amount of probe cleavage.

Well-designed TaqMan® probes require very little optimization. In addition, they can be used for multiplex assays by designing each probe with a spectrally unique fluor/quench pair. However, TaqMan® probes can be expensive to synthesize, with a separate probe needed for each polynucleotide target being analyzed.

Any suitable reporter dye can be used with the methods and compositions of the present invention. Suitable reporter dyes include, but are not limited to, 6FAM (Excitation Max at 495, Emission Max at 522), 5-FAM (Excitation Max at 494, Emission Max at 530), TET(Excitation Max at 521, Emission Max at 538), HEX (Excitation Max at 535, Emission Max at 553), JOE (Excitation Max at 528, Emission Max at 554), VIC (Excitation Max at 538, Emission Max at 554), and NED (Excitation Max at 546, Emission Max at 575).

Any suitable quencher can be used with the methods and compositions of the present invention. Suitable quencher include, but are not limited to, MGBNFQ and TAMARA.

In one embodiment, the probe contains a 5' FAM-labeled Reporter dye (6-Carboxyfluorescein (FAM)), that has an Excitation Max of 495 nm and an Emission Max at 520 mn, and a 3' MGBNFQ Quencher (Minor groove binder/Non-fluorescent quencher).

Molecular Beacons

Like TaqMan® probes, Molecular Beacons also use FRET to detect and quantitate the synthesized PCR product via a fluor coupled to the 5' end and a quench attached to the 3' end of an oligonucleotide substrate. Unlike TaqMan® probes, Molecular Beacons are designed to remain intact during the amplification reaction, and must rebind to target in every cycle for signal measurement. Molecular Beacons form a stem-loop structure when free in solution. Thus, the close proximity of the fluor and quench molecules prevents the probe from fluorescing. When a Molecular Beacon hybridizes to a target, the fluorescent dye and quencher are separated, FRET does not occur, and the fluorescent dye emits light upon irradiation. Molecular Beacons, like TaqMan® probes, can be used for multiplex assays by using spectrally separated fluor/quench moieties on each probe. As with TaqMan® probes, Molecular Beacons can be expensive to synthesize, with a separate probe required for each target.

Scorpions

With Scorpion probes, sequence-specific priming and PCR product detection is achieved using a single oligonucleotide. The Scorpion probe maintains a stem-loop configuration in the unhybridized state. The fluorophore is attached to the 5' end and is quenched by a moiety coupled to the 3' end. The 3' portion of the stem also contains sequence that is complementary to the extension product of the primer. This sequence is linked to the 5' end of a specific primer via a non-amplifiable monomer. After extension of the Scorpion primer, the specific probe sequence is able to bind to its complement within the extended amplicon thus opening up the hairpin loop. This prevents the fluorescence from being quenched and a signal is observed.

SYBR Green

SYBR Green provides the simplest and most economical format for detecting and quantitating PCR products in real-time reactions. SYBR Green binds double-stranded DNA, and upon excitation emits light. Thus, as a PCR product accumulates, fluorescence increases. The advantages of SYBR Green are that it is inexpensive, easy to use, and sensitive. The disadvantage is that SYBR Green will bind to any double-stranded DNA in the reaction, including primer-dimers and other non-specific reaction products, which results in an overestimation of the target concentration. For single PCR product reactions with well designed primers, SYBR Green works extremely well.

Real-time Reporters for Multiplex PCR

TaqMan® probes, Molecular Beacons and Scorpions allow multiple DNA species to be measured in the same sample (multiplex PCR), since fluorescent dyes with different emission spectra may be attached to the different probes. Multiplex PCR allows internal controls to be co-amplified and permits allele discrimination in single-tube, homogeneous assays. These hybridization probes afford a level of discrimination impossible to obtain with SYBR Green, since they will only hybridize to true targets in a PCR and not to primer-dimers or other spurious products.

Quantitation of Results

Two strategies are commonly employed to quantify the results obtained by real-time RT-PCR; the standard curve method and the comparative threshold method. These are discussed briefly below.

Standard Curve Method

In this method, a standard curve is first constructed from a target oligonucleotide of known concentration. This curve is then used as a reference standard for extrapolating quantitative information for oligonucleotides of unknown concentrations.

In addition to the target modified oligonucleotide, other nucleic acid samples can be used to construct the standard curve, including purified plasmid dsDNA, in vitro generated ssDNA or any cDNA sample expressing the target gene. Spectrophotometric measurements at 260 nm can be used to assess the concentration of these DNAs, which can then be converted to a copy number value based on the molecular weight of the sample used. cDNA plasmids are the preferred standards for standard curve quantitation.

Comparative Ct Method

Another quantitation approach is termed the comparative Ct method. This involves comparing the Ct values of the samples of interest with a control or calibrator such as a non-treated sample or RNA from normal tissue. The Ct values of both the calibrator and the samples of interest are normalized to an appropriate endogenous housekeeping gene.

For the delta Ct calculation to be valid, the amplification efficiencies of the target and the endogenous reference must be approximately equal. This can be established by looking at how delta Ct varies with template dilution. If the plot of oligonucleotide dilution versus delta Ct is close to zero, it implies that the efficiencies of the target and reference are very similar. If a reference gene cannot be found whose amplification efficiency is similar to the target, then the standard curve method is preferred.

Instrumentation for Real-Time PCR

Real-time PCR requires an instrumentation platform that consists of a thermal cycler, a computer, optics for fluorescence excitation and emission collection, and data acquisition and analysis software. These machines, available from several manufacturers, differ in sample capacity (some are 96-well standard format, others process fewer samples or require specialized glass capillary tubes), method of excitation (some use lasers, others broad spectrum light sources with tunable filters), and overall sensitivity. There are also platform-specific differences in how the software processes data.

Commercial kits for performing Real-Time RT-PCR include, e.g., Ambion's MessageSensor™ RT Kit. This kit includes an RNase H+ MMLV RT that clearly outperforms MMLV RT enzymes that have abolished RNase H activity in real-time RT-PCR experiments. Unlike many other qRT-PCR kits, MessageSensor includes a total RNA control, a control human GAPDH primer set, RNase inhibitor, and nucleotides, as well as a buffer additive that enables detection with SYBR® Green dye. In addition to the specific products described above, Ambion offers SuperTaq™ Polymerase, M-MLV Reverse Transcriptase, and RNase-free PCR tubes. To prevent cross contamination during PCR experiments, Ambion also offers DNAZap™ DNA Degradation Solution and RNase-free barrier pipette tips.

Magnetic Particle Processor

Sample preparation using magnetic particles may be performed manually or may be performed automatically using automated magnetic particle processors. Commercial particle movers include the Dynal MPC® Magnetic Particle Concentrator (Dynal Biotech Cat # MPC-S, Brown Deer, Wis.). Dynal MPC-S is a tool to separate magnetic beads from liquid samples. Magnetic beads are attracted to the magnet adjacent to the tube wall when the tube is inserted into the Dynal MPC-S housing and the magnetic slide is inserted. This enables easy removal of supernatant. The Magnetic beads are left isolated in the tube. Commercial magnetic particle processors include KingFisher® processing technology (Thermo Labsystems; Vantaa, Finland; see for example U.S. Pat. No. 6,596,162 and PCT Publication No. WO 01/68263A1). KingFisher® 96 magnetic particle processor automates sample preparation processes of nucleic acids, proteins and cells in a 96-well plate format.

Kits

The present invention provides kits that can be used in the above methods. In one embodiment, a kit comprises a first (capture probe) and a second (detector probe) polynucleotide, each having complementarity to a non-overlapping portion of a selected target oligonucleotide (e.g., a VEGF aptamer). The kit optionally further includes a tag (e.g., a magnetic bead) joined, or ready to be joined, to the first polynucleotide. The kit may further include buffers for hybridization of the first and second polynucleotides to the target oligonucleotide. The kit may still further include buffers, e.g., for washing, and/or REAL TIME-PCR. Optionally, the kit further includes means for ligating the first and second polynucleotides (e.g., a ligase enzyme such as T4 DNA ligase). In certain embodiments, the kit further includes components for the REAL TIME-PCR-mediated detection and/or quantification of the detector probe, including forward and reverse PCR primers corresponding to an amplifiable sequence present on the second polynucleotide (detector probe), as well as a detection probe (e.g., a TaqMan® probe having the general structure: 6FAM-XXX-MGBNFQ, wherein "XXX" is a sequence of about 10-20 or more nucleotides corresponding to the amplifiable sequence of the detection probe.

EXAMPLES

The following examples serve to illustrate certain useful embodiments and aspects of the present invention and are not to be construed as limiting the scope thereof. Alternative materials and methods can be utilized to obtain similar results.

Reagents and Chemicals

The following reagents and chemicals were used in the dual hybridization assay: Pegaptanib, Macugen® EYE001 (Eyetech Pharmaceuticals; New York, N.Y.); Capture Probe (21 mer Biotin-Oligo primer) (Sigma Genosys; Chicago, Ill.); Detection Probe (21mer Digoxigenin-Oligo primer); (Sigma Genosys; Chicago, Ill.); Anti-Digoxigenin-AP (Roche Biochemicals Cat # 1093274, Indianapolis, Ind.); Rnase, Dnase free water (ICN Biomedicals, Cat # 821739, Irvine, Calif.); Sodium Chloride (Sigma Cat # S-9888, St. Louis, Mo.); Trizma base (Sigma Cat # T-1503, St. Louis, Mo.); Trizma hydrochloride (Sigma Cat # T-6666, St. Louis, Mo.); EDTA, disodium salt (Sigma Cat # ED2P, St. Louis, Mo.); Human EDTA Plasma; 20×SSC Buffer (Ambion Cat # 9763, Austin, Tex.); 30% Sodium-N-lauroyl-Sarkosyl solution (Fluka Cat # 61747, St. Louis, Mo.); Tween 20 (Sigma Cat # P-7949); SuperBlock Blocking Solution in TBS (Pierce Cat # 37535 Rockford, Ill.); AttoPhhos Flourescent Substrate for AP (Promega Cat # S 1000 (S1011 for substrate only), Madison, Wis.). Other equivalent reagents from alternative suppliers may be substituted for any of the above listed reagents.

Materials and Equipment

The following reagents and chemicals were used in the dual hybridization assay: Dynabeads® M270 epoxy magnetic beads (Dynal Biotech Cat # 143.01, Brown Deer, Wis.); Dynabeads® M270 carboxylic acid magnetic beads (Dynal Biotech Cat # 143.05 and 143.06, Brown Deer, Wis.); Magnetic particle mover (Dynal Biotech Cat # MPC-S (Magnetic Particle Concentrator, type-S), Brown Deer, Wis.); KingFisher® 96 magnetic particle processor (Thermo Labsystems, Cat # 540 05 00, Milford, Mass.); KingFisher 96 KF plate (Thermo Labsystems, Cat # 970 02 540, Milford, Mass.); KingFisher 96 Deep Well tips (Thermo Labsystems, Cat # 970 02 530, Milford, Mass.); 200 µl PCR tubes (ISC-BioExpress Cat # T-3035-1, Kaysville, Utah) Rapid DNA Ligation Kit (Roche Cat # 1635379, Indianapolis, Ind.); MJ Tetrad PCR Thermal Cycler (or any other suitable PCR Thermal Cycler); Pipette tips, various sizes (VWR); Microcentrifuge tubes, 1.5 ml (Costar 3207, VWR Cat# 29442-580); Polypropylene tubes with caps (50 ml); Rainin adjustable pipette (1 ml-20 ml); Rainin adjustable pipette (10 ml-100 ml); Rainin adjustable pipette (100-1000 ml); Equivalent materials and equipment from alternative suppliers may be substituted for any of the items listed above.

Example 1

Antibody-Based Detection of Anti-VEGF Aptamer (Pegaptanib)

This example of a dual hybridization assay is a quantitative assay that is an antibody-based method used to detect the pegaptanib aptamer in human EDTA plasma. Pegaptanib in human EDTA plasma samples is mixed with two complementary oligonucleotides (oligos). One of the oligos (a capture oligo) is labeled with biotin permitting capture of the complex on a microtiter plate pre-coated with NeutrAvidin. The second is a detection oligo labeled with digoxigenin. The pegaptanib/oligo mixture is heated to 75° C., and incubated at 37° C. for annealing of the oligos to pegaptanib. Then, the mixture is transferred into a NeutrAvidin-coated plate for capture of the complex and its detection with an alkaline phosphatase labeled anti-digoxigenin antibody. AttoPhos is used as the substrate for a fluorescent readout. Sample concentrations are determined by interpolation from the standard curve, which has been fit using a 4-parameter logistic equation. The reaction is performed in a sample volume of 100 µl. The calibration range is from 2.00 to 256 ng/ml. The range of quantification is from 8.00 to 256 ng/ml Samples are stored at a nominal temperature of −20° C. or below.

Example 2

PCR Dual Hybridization-Based Detection of Nucleic Acids: Preliminary Procedures

Reagent Preparation:

Hybridization Buffer (6×SSC/1.0% sarkosyl) is prepared; and 150 ml 20×SSC and 16.7 ml 30% Sarkosyl is mixed and the volume adjusted to 500 ml with distilled water ($dH_2O$) (can be stored at 4° C.).

The wash buffer 4× concentrate is 80 mM Tris Base, 0.6M NaCl and 0.4% Tween 20). This solution is prepared as follows: dissolve 9.69 g Tris base and 35.06 g NaCl in 1 liter of $dH_2O$; add 4.0 ml Tween 20 and mix thoroughly; and store at room temperature. The 1× wash buffer is 20 mM Trise Base, 150 mM NaCl and 0.1% Tween 20) and is made by diluting 4× concentrate wash buffer by mixing 250 ml buffer and 750 mL $dH_2O$ and is stored at room temperature.

Oligonucleotide 100 mM stock solutions are made by resuspending oligos in $H_2O$ to yield a 100 mM stock concentration. The stock solution is aliquoted at 30.0 ml oligo per tube and stored at −20° C.

Preparation of Samples, Stock Standard, Calibration Standards, and Quality Controls:

A stock standard is prepared by reconstituting lyophilized pegaptanib in RNase- & DNase-free water to make stock solution. This stock standard is aliquoted into RNase- & DNase-free polypropylene tubes and stored in aliquots at −20° C. or below.

To prepare the calibration standards, an aliquot of stock standard is thawed and spiked into appropriate tissue or water. The concentrations for the individual calibration standard curve points for pegaptanib are: 1000 nM, 500 nM, 250 nM, 100 nM, 25 nM, 5 nM, 1 nM, 0.2 nM, 0.04 nM, 0.008 nM, 0.0016 nM, and 0 nM. The concentrations for the controls are 400 nM, 40 nM, 0.4 nM. For testing of other the other nucleic acids the concentrations for the individual calibration standard curve points are 100 nM, 25 nM, 5 nM, 1 nM, 0.2 nM, 0.04 nM, and 0.008 nM while the concentrations for the controls are 50 nM, nM, and 0.5 nM.

To prepare the primers, thaw 100 µM primer, Prepare Primer Mix (at 100 nM), and dilute stock 1:1000 in Hybridization buffer (165 µl primer mix per sample duplicate).

To prepare the quality control pools, an aliquot of stock standard is thawed and spiked into appropriate tissue. Recommended QC concentrations are 25.00 and 0.25 ng/ml. Sample preparation and assay procedure were as described below.

The capture primer-coated M-270 epoxy magnetic beads (capture beads) were prepared by: re-suspending 3 mg of M270 epoxy magnetic beads in 500 µl of 1×PBS; washing by pulling down with MPC-S, removing supernatant, and repeating; removing the tube from MPC-S, and re-suspending beads in 360 µl of primer mix comprising 60 µg of capture primer in 240 µl 1×PBS and 120 µl 3M sodium acetate; incubating overnight on rotator; capturing beads and removing supernatant; re-suspending in 500 µl of 1×PBS (repeated twice); and, finally, re-suspending beads in a final volume of 576 µl (this is considered 1×).

The capture primer-coated M-270 carboxylic acid magnetic beads (capture beads; Dynabeads®) were prepared by the one-step coating procedure (Step 3.1a) found in the Dynabeads M-270 carboxylic acid package insert: 1) Mix ligand and Dynabeads; 2) Add carbodiimide and incubate the reaction mixture; and 3) Wash the Dynabeads and resuspend in buffer. Coat at 4° C. overnight at 30 mg of bead per ml. The next day, use 1×PBS or Hybridization buffer to bring up to 5.5 mg of bead per ml. The traditional procedure for ligand coupling is the formation of an amide bond between a primary amino group of the ligand and the carboxylic acid groups on the surface of the Dynabeads, mediated by carbodiimide activation. The intermediate product of the reaction between the carboxylic acid and the carbodiimide is very labile and will hydrolyse quickly. Alternatively, the activated Dynabeads can be captured as a less labile intermediate, such as an N-hydroxyl succinimide ester (NHS, MW 115.1 or sulfo-NHS, MW 217.1).

Cell Lysis:

To obtain the cell lysis, a Qiagen RNeasy Protect Mini Kit (catalog # 74124) is used following the instructions in the manual provided. There is no need to isolate the RNA from the cell lysis. The RNeasy Kit includes RNAlater RNA Stabilization Reagent (50 ml), 50 RNeasy Mini Spin Columns, Collection Tubes (1.5 ml and 2 ml), RNase-free Reagents and Buffers (see U.S. Pat. No. 5,234,809 and European Patent No. 0,389,063,).

Tissue digestion:

Homogenize the rabbit eye tissue by enzyme digestion as follows: add 500-1500 µl of 1×PBS depending on the size of the tissue, 5 µl of each of four Hyaluronidases by Sigma Aldrich (catalog # H-4272, H-3757, H-3506, H-3631), 20 µl of Blendzyme (Roche/Boehringer catalog # 1814176; Liberase Blendzymes are mixtures of highly purified collagenase and neutral protease enzymes, formulated for efficient, gentle, and reproducible dissociation of tissue from a wide variety of sources), and 10 µl of DNAse (Roche catalog # 776785). Mix thoroughly and incubate overnight at 37° C. The next day add 20 µl of Proteinase K (Sigma catalog P-6556) and incubate the specimen at 65° C. for 2 hrs. The tissue is now ready for analysis.

Example 3

PCR Dual Hybridization-Based Detection of Anti-VEGF Aptamer (Pegaptanib)

Oligonucleotide Sequences:
The target oligonucleotide, EYE001 has the structure:

(SEQ ID NO:1)
PEG-linker-$C_fG_mG_mA_rA_rU_fC_fA_mG_mU_fG_mA_m$-$A_mU_fG_mC_fU_fU_fA_m$ $U_fA_mC_fA_mU_fC_fC_fG_m$3'-3'-$T_d$.

Capture Probe 100 mM, 21 mer 5'-Amine-labelled Oligonucleotide primer (Invitrogen, Carlsbad, Calif.):

(SEQ ID NO:4)
5'-Amine-AAAACGGATGTATAAGCATTCACTGATTCCG-3';

Detection Probe 100 mM, 72 mer 5'-Phophate-labelled Oligonucleotide primer (Invitrogen, Carlsbad, Calif.):

(SEQ ID NO:6)
5'-Phos-TTCACTGATTCCGAGAGAACAGTGTCACGGTTAAAGGATAAG

GAACTCTTCTGGAATGACTTTGCGGGCTGTTGACGA-3'.

Assay Procedure:

First, prepare calibration standards, quality controls, and samples at room temperature. Next, dispense 25 µl of calibrators, controls, and unknowns into the appropriate 0.2 ml PCR tube. Add 165 µl of 1 nM of detection primer to each calibrator, control and unknown. Then add 5 µl of capture beads for Macugen detection (10 µl if detecting other nucleic acids) to each calibrator, control and unknown. Place the PCR tubes in a Thermal Cycler programmed to run at 75° C. for 15 minutes (for other nucleic acids run at 95° C.), 37° C. for 1 hr, and to ramp down to 25° C. at 0.1° C./second.

Manual Bench Method:

Re-suspend magnetic beads in 500 µl of 1× wash buffer and let incubate at room temperature for 5 min. Capture beads on MPC-S and remove supernatant (repeat three times). Then re-suspend beads in 100 µl of 1× ligation buffer and transfer to fresh 1.5 ml tube. Next, capture beads on MPC-S and re-suspend in 30 µl of ligation mixture: per reaction add 15 µl 1× ligation buffer, 15 µl 2× ligation buffer and 1 µl of ligase, and incubated at room temperature for 30 min. This is then re-suspended in 500 ul of 1× wash buffer and incubate at 75° C. for 5 min. The beads are captured on MPC-S and the supernatant removed (this wash is repeated seven times). Finally, re-suspend the beads in 100 µl of H₂O.

Automated Method (Without Ligation):

At the end of the Thermal Cycler program, transfer 140 µl of each sample into the appropriate well of a KingFisher 96 KF plate. Place the plate in a King Fisher programmed to wash the beads 5 times with 200 µl of 1× buffer and ultimately dispense the washed beads into 100 µl of deionized water.

Automated Method (With Ligation):

At the end of the Thermal Cycler program, transfer 140 µl of each sample into the appropriate well of a KingFisher 96 KF plate. Place the plate in a King Fisher which is programmed to do the following: The beads are washed twice with 200 µl of 1× buffer and once with 100 µl of 1× ligation buffer. They are then incubated in 50 µl of ligation mix (ligation mix contains 25 µl of 1× ligation buffer, 25 µl 2× ligation buffer and 1 µl of ligase enzyme) for 30 minutes. At the end of the 30 minutes, the King Fisher will pause to allow the manual addition of 150 µl of 1× wash buffer to the ligation plate (The ligation mixture contains glycerol; adding 1× wash buffer ensures appropriate transfer of the beads to the next plate.) Next, the beads are washed seven times at 75° C. with 200 µl of 1× wash buffer. After it is done washing the beads, it will dispense them into a plate containing 100 µl of deionized water.

TaqMan® Procedure:

First, set up the following PCR cocktail per sample: 1 µl H2O, 12.5 µl 2× TaqMan® PCR mix, 0.125 µl Forward PCR Primer, 0.125 µl Reverse PCR Primer, and 1.25 µl Probe. (Primers and probe can be varied depending upon the experiment)

The PCR (TaqMan®) Dual Hybridization Primer/Probe set includes:

```
                                             (SEQ ID NO:9)
Probe- 6FAM- AAG GAA CTC TTC TGG AAT GA- MGBNFQ;

(SEQ ID NO:10)
Forward Primer- GAG AAC AGT GTC ACG GTT AAA GGA;
and (SEQ ID NO:11)
Reverse Primer- CGT CAA CAG CCC GCA AA.
```

Next, add 15 µl of the above PCR cocktail to a TaqMan® optical tube in a 96-well plate format, and add 10 µl of sample to each optical tube and close with cap. Then, place PCR reactions in TaqMan® and use the following PCR set up: 50° C. for 2 minutes, 95° C. for 10 minutes, and 40 cycles of 95° C. for 15 seconds followed by 60° C. for 1 minute. Finally, the TaqMan® data is analyzed.

Data Processing:

Sample concentrations are determined by interpolation from the standard curve that has been fit using a 4-parameter logistic equation.

Figure 10:
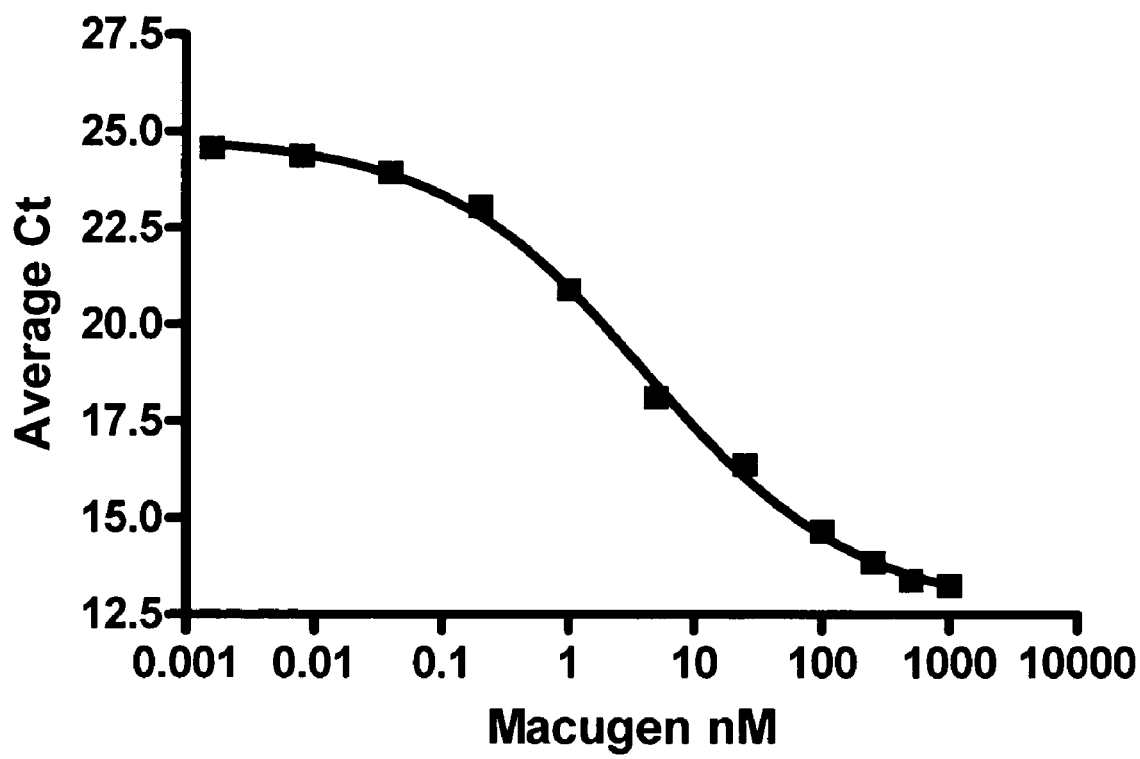
FIG. 10 is a graph representing a standard curve for determining the amount of pegaptanib in a sample.

Results:

The average Ct value of a sample containing the pegaptanib was determined to be 19.406 (see Table 1(B)). Interpolation from the pegaptanib standard curve as illustrated in Table 1(A) and FIG. 10 determined that 2.7 nM of the pegaptanib was present in the sample.

TABLE 1(A)

| Macugen nM | Average Ct |
|---|---|
| 1000 | 13.255 |
| 500 | 13.397 |
| 250 | 13.861 |
| 100 | 14.654 |
| 25 | 16.375 |
| 5 | 18.103 |
| 1 | 20.891 |
| 0.2 | 23.052 |
| 0.04 | 23.932 |
| 0.008 | 24.372 |
| 0.0016 | 24.571 |
| 0 | 26.816 |

TABLE 1(B)

| Dilution | Ct Dup1A | Ct Dup1B | Ct Dup2A | Ct Dup2B | Ave Ct | SD | CV % | PRISM |
|---|---|---|---|---|---|---|---|---|
| None | 19.358 | 19.089 | 19.235 | 19.941 | 19.406 | 0.374 | 1.925 | 2.7 |

Example 4

Detection and Quantitation of a Pegaptanib Using QC Primer

Figure 7:
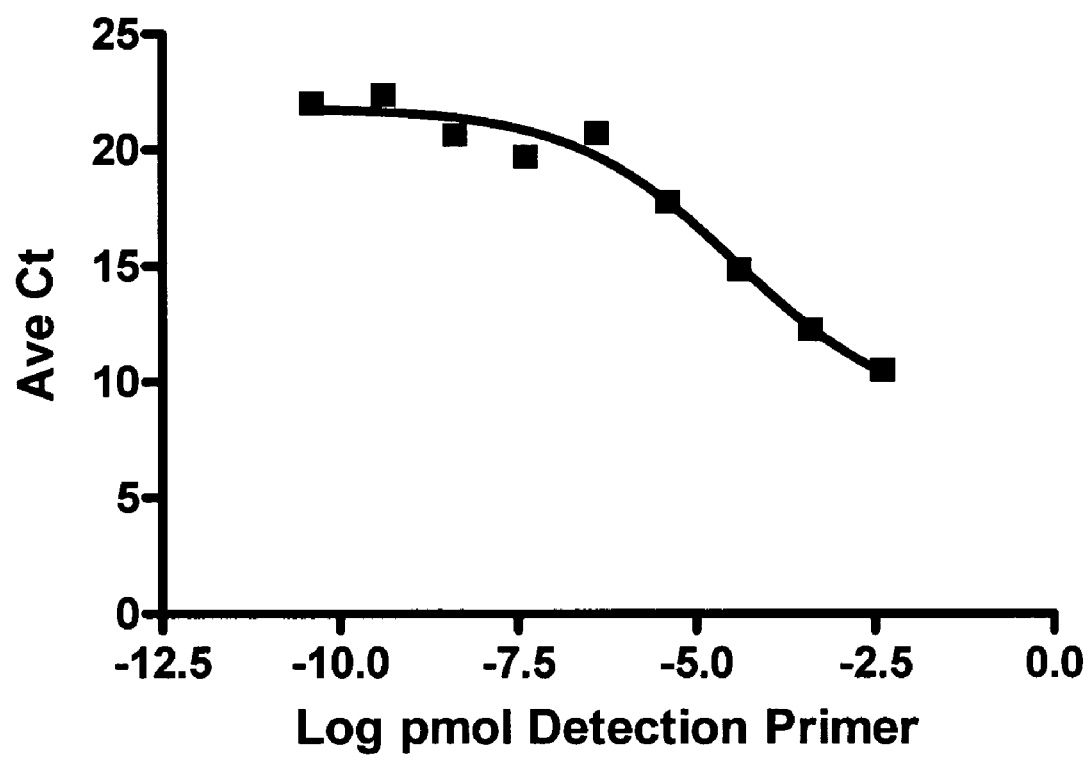
FIG. 7 is a graph representing a standard curve for determining the amount of detection primer.

Using the general procedure as described in Example 3, modified to include a capture primer comprising a Taqman® detection site for use as a quality control (QC) primer. A standard curve for the capture primer was prepared. The resulting standard curve is shown in Table 2(A) and FIG. 5. A standard curve for a detection primer for quantitating pegaptanib was prepared. The resulting standard curve is shown in Table 2(c) and FIG. 7.

Beads:

A carboxylic acid bead was coupled to the following capture probe sequence

```
(5' to 3'):
                                            (SEQ ID NO:12)
Amino - AAA CTC CGT GGG ACG AGT GAT ACA GTG CCA

GAG CAA TTG GAC TAC GCT AAA CGG CGT ATG GCT GAA

AAA CGG ATG TAT AAG CA.
```

The PCR (TaqMan®) Dual Hybridization Primer/Probe set includes:

```
                                            (SEQ ID NO:14)
QC Probe-6FAM-CCA GAG CAA TTC GAC-MGBNFQ;

(SEQ ID NO:15)
Forward Primer- CTC CGT GGG ACG AGT GAT ACA;
and (SEQ ID NO:16)
Reverse Primer- TCA GCC ATA CGC CGT TTA GC.
```

Figure 5:
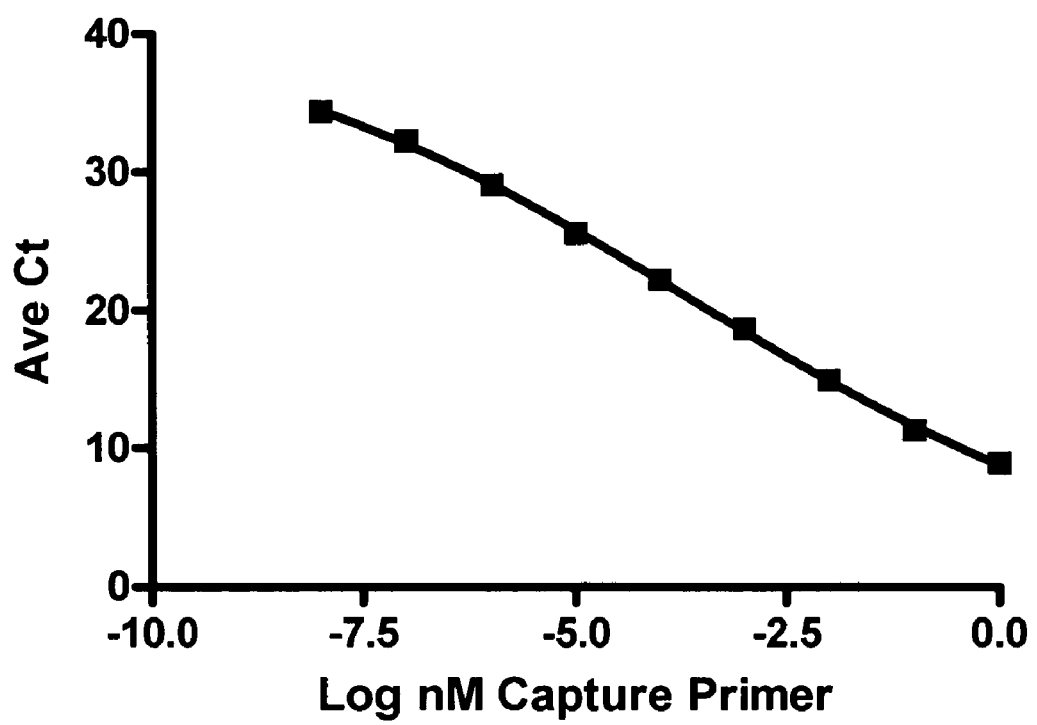
FIG. 5 is a graph representing a standard curve for determining the amount of capture primer that is coated onto a magnetic bead.

Results:

The capture primer covalently bound to the magnetic bead was quantitated by performing RT-PCR (Taqman®) on a sample of a QC capture primer-coated magnetic beads after the coating process and extrapolating the Ct value off of a standard curve generated by detecting known quantities of the QC capture primer in solution. The average Ct value of the QC capture primer-coated magnetic beads was determined to be 9.36 (see Table 2(A)). Interpolation from the QC capture primer standard curve as illustrated in FIG. 5 determined that 18.15 nM of the QC-capture primer was present on the coated magnetic beads.

Table 2(A)

| nM Capture Primer | Ave Ct | Bead | Ave Ct | Extrapolated Value nM |
|---|---|---|---|---|
| 1 | 11.366 | 1/100 dilution | 14.021 | 18 |
| 0.1 | 14.971 | | | |
| 0.01 | 18.716 | | | |
| 0.001 | 22.207 | | | |
| 0.0001 | 25.540 | | | |
| 0.00001 | 29.082 | | | |
| 0.000001 | 32.266 | | | |
| 0.0000001 | 34.373 | | | |

The average Ct value of a sample containing the pegaptanib was determined to be 17.47 (see table 2(B)). Interpolation from the pegaptanib standard curve as illustrated in Table 2(C) and FIG. 7 determined that 0.0001 µmol of the pegaptanib was present in the NIH 3T3 cell lysis. The percent hybridization of pegaptanib was calculated to be 0.03% (see Table 2(D)).

TABLE 2 (B)

| nM Macugen | Ct Dup1A | Ct Dup1B | Ct Dup2A | Ct Dup2B | Ave Ct | SD | pmol Detected Detection Primer | Total pmol Macugen Detected |
|---|---|---|---|---|---|---|---|---|
| 25 | 17.64 | 17.49 | 17.38 | 17.40 | 17.477 | 0.12 | 0.00000525 | 0.0001313 |

TABLE 2 (C)

| pmol of Detection primer | Ave Ct |
|---|---|
| 0.004 | 10.52 |
| 0.0004 | 12.28 |
| 0.00004 | 14.89 |
| 0.000004 | 17.78 |
| 0.0000004 | 20.73 |
| 0.00000004 | 19.73 |
| 0.000000004 | 20.66 |
| 0.0000000004 | 22.37 |
| 0.00000000004 | 22.01 |

TABLE 2 (D)

| pmol Macugen | Ct | Detected pmol Macugen | % Hybridized Macugen |
|---|---|---|---|
| 0.625 | 17.48 | 0.0001 | 0.02 |

Figure 6:
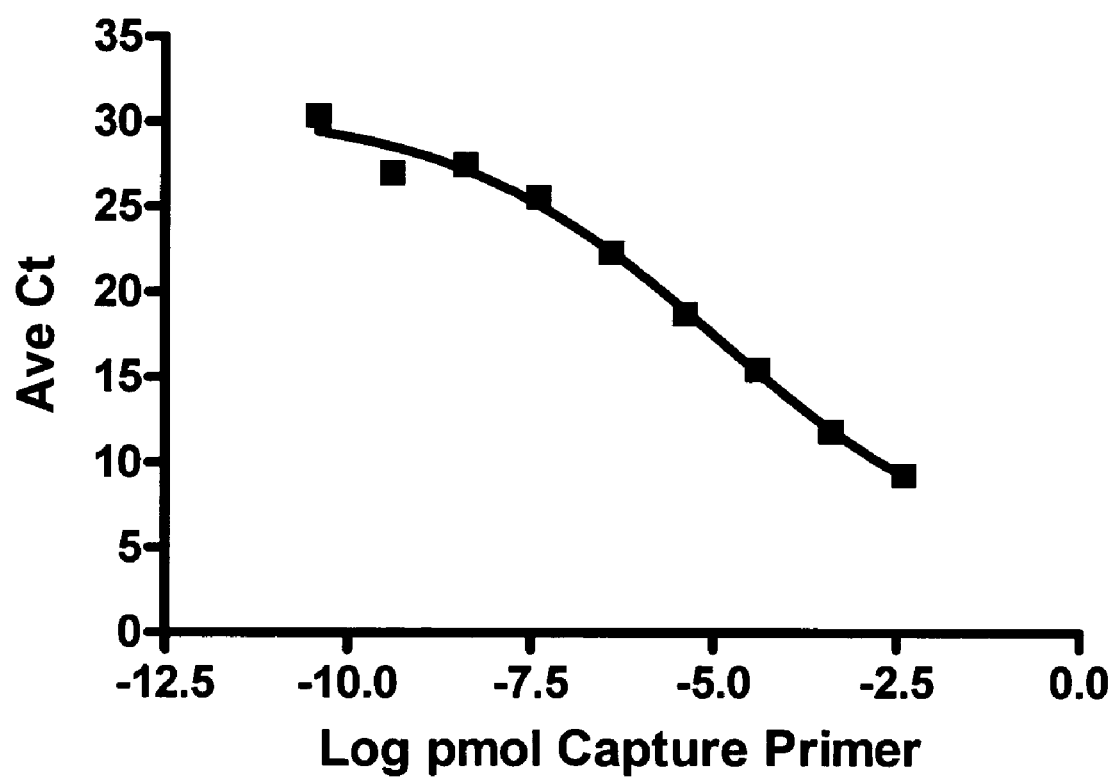
FIG. 6 is a graph representing a standard curve for determining the amount of capture primer that is available following a washing procedure.

A capture primer standard curve is illustrated in Table 2(E) and FIG. 6.

TABLE 2 (E)

| pmol of Capture primer | Ave Ct |
|---|---|
| 0.004 | 9.27 |
| 0.0004 | 11.83 |
| 0.00004 | 15.44 |
| 0.000004 | 18.70 |
| 0.0000004 | 22.33 |
| 0.00000004 | 25.59 |
| 0.000000004 | 27.48 |
| 0.0000000004 | 27.00 |
| 0.00000000004 | 30.335 |

Example 5

Detection and Quantitation of a VEGF Antisense Nucleic Acid

Using the general procedure as described in Example 3, the following VEGF antisense nucleic acid sequence was detected and quantitated (5' to 3'): CAC CCA AGA CAG CAG AAA G (SEQ ID NO: 17). A Standard Curve for the VEGF Antisense nucleic acid sequence was prepared. The resulting standard curve is shown in Table 3(A) and FIG. 7.

Samples:

Cell lysis of VEGF Antisense nucleic acid transfected in NIH 3T3 cells. The following Hybridization Buffer was used: 6×SSC, 1% Sarkosyl. 1× Wash Buffer in autoclaved water. Sample cell lysis were diluted 1/10 with Distilled Water to make 1× Cell lysis.

Beads:

A carboxylic acid bead was coupled to the following capture probe sequence (5' to 3'): Amino-AAC TTT CTG CTG (SEQ ID NO: 20).

Detection Primer:

VEGF Antisense detection probe sequence (5' to 3'): TCT TGG GTG AGA GAA CAG TGT CAC GGT TAA AGG ATA AGG AAC TCT TCT GGA ATG ACT TTG CGG GCT GTT GAC GA (SEQ ID NO: 21) was diluted to 100 nM for assay in DEPC water.

Results

The average Ct value of the sample containing the VEGF antisense nucleic acid was determined to be 19.70 (see Table 3(B)). Interpolation from the VEGF Antisense standard curve as illustrated in Table 3(A) and FIG. 7 determined that 14.9 nM of the VEGF antisense nucleic acid was present in the NIH 3T3 cell lysis.

TABLE 3(A)

| nM | Ct Dup1A | Ct Dup1B | Ct Dup2A | Ct Dup2B | Ave Ct | SD | CV % | Observed nM | % Deviation |
|---|---|---|---|---|---|---|---|---|---|
| 100 | 15.78 | 15.60 | 16.02 | 15.68 | 15.77 | 0.18 | 1.15 | 76 | 24 |
| 50 | 15.83 | 15.90 | 16.03 | 15.96 | 15.93 | 0.09 | 0.54 | 56 | −11 |
| 25 | 16.23 | 16.18 | 16.50 | 16.52 | 16.35 | 0.18 | 1.09 | 29 | −15 |
| 5 | 17.98 | 18.14 | 18.14 | 18.09 | 18.09 | 0.08 | 0.42 | 5 | 0 |
| 1 | 20.17 | 20.40 | 20.28 | 20.32 | 20.29 | 0.10 | 0.49 | 1 | 3 |
| 0.2 | 22.20 | 22.33 | 22.67 | 22.36 | 22.39 | 0.20 | 0.89 | 0.171 | 14 |
| 0.04 | 23.29 | 23.04 | 23.10 | 23.14 | 23.14 | 0.11 | 0.46 | | |
| 0.008 | 24.20 | 24.29 | 24.60 | 24.46 | 24.39 | 0.18 | 0.72 | | |
| 0 | 24.12 | 23.99 | 25.78 | 25.75 | 24.91 | 0.99 | 3.98 | | |

TABLE 3 (B)

| Dilution | Ct Dup1A | Ct Dup1B | Ct Dup2A | Ct Dup2B | Ave Ct | SD | CV % | Observed nM | Observed nM × dilution factor |
|---|---|---|---|---|---|---|---|---|---|
| 1/10 | 19.74 | 19.80 | 19.73 | 19.53 | 19.70 | 0.12 | 0.59 | 1.49 | 14.9 |

Example 6

Detection and Quantitation of a RNAi Nucleic Acid

Figure 8:
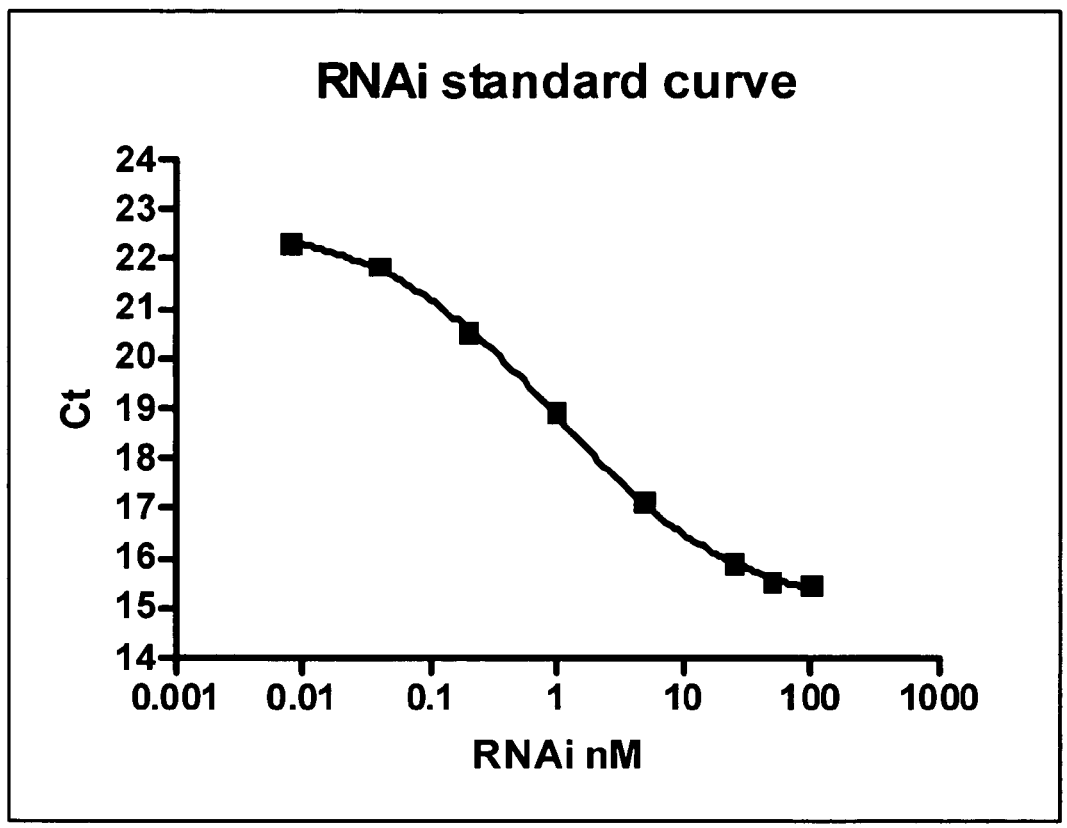
FIG. 8 is a graph representing a standard curve for determining the amount of RNAi in a sample
Figure 9:
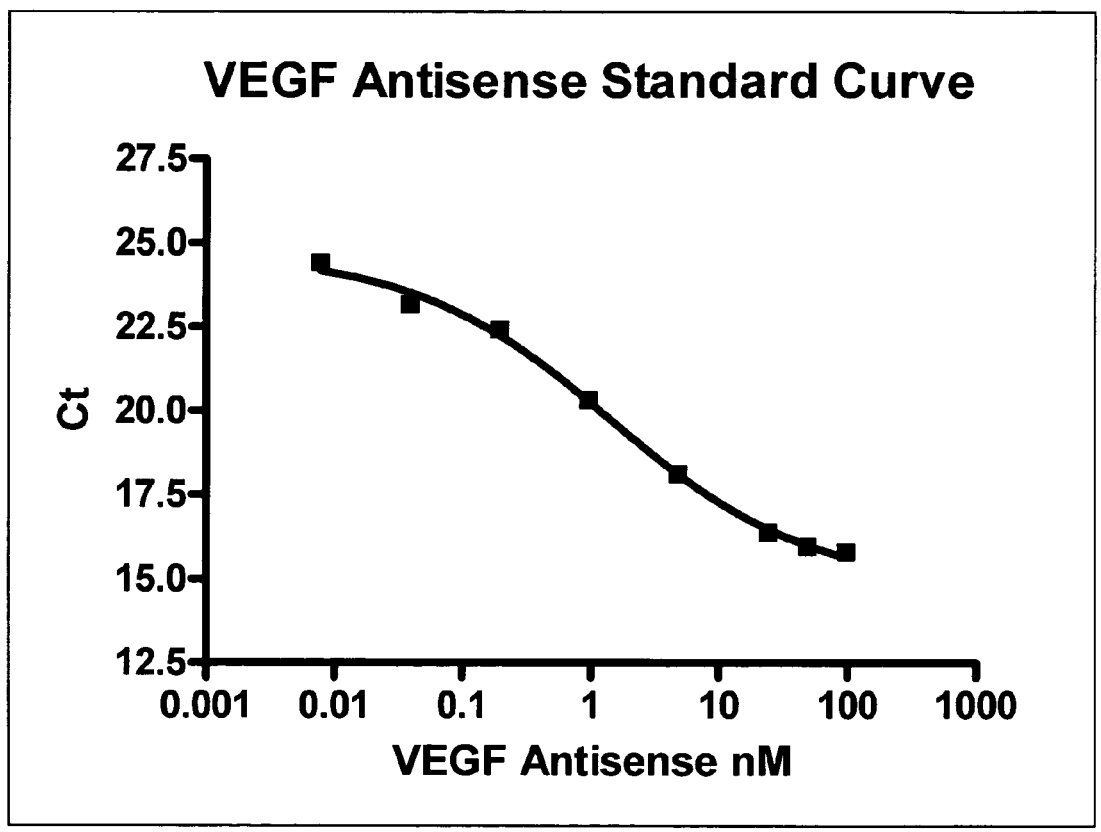
FIG. 9 is a graph representing a standard curve for determining the amount of Antisense nucleic acid in a sample.

Using the general procedure as described in Example 3, the following RNAi nucleic acid sequence was detected and quantitated (5' to 3' UUG CAC AUU GCU CAG UUC AUA CAC C (SEQ ID NO: 18). The sequence was supplied with the following RNAi antisense strand (5' to 3'): GGU GUA UGA ACU GAG CAA UGU GCA A (SEQ ID NO: 19). A Standard Curve for the RNAi nucleic acid sequence was prepared. The resulting standard curve is shown in Table 4(A) and FIG. 8.

Samples:

Cell lysis of VEGF Antisense nucleic acid transfected in NIH 3T3 cells. The following Hybridization Buffer was used: 6×SSC, 1% Sarkosyl. 1× Wash Buffer in autoclaved water. Sample cell lysis were diluted 1/10 with Distilled Water to make 1× Cell lysis.

Beads:

A carboxylic acid bead was coupled to the following capture probe sequence (5' to 3'):

```
                                        (SEQ ID NO:22)
        Amino- AAG GTG TAT GAA CTG.
```

Results:

The average Ct value of the sample containing the RNAi nucleic acid was determined to be 19.85 (see Table 4(B)). Interpolation from the VEGF Antisense standard curve as illustrated in Table 4(A) and FIG. 8 determined that 41.7 nM of the RNAi nucleic acid was present in the NIH 3T3 cell lysis.

Detection Primer:

RNAi detection probe sequence (5' to 3'): AGC AAT GTG CAA AGA GAA CAG TGT CAC GGT TAA AGG ATA AGG AAC TCT TCT GGA ATG ACT TTG CGG GCT GTT GAC GA (SEQ ID NO: 23) was diluted to 100 nM for assay in DEPC water.

TABLE 4 (A)

| nM | Ct Dup1A | Ct Dup1B | Ct Dup2A | Ct Dup2B | Ave Ct | SD | CV % | Observed nM | % Deviation |
|---|---|---|---|---|---|---|---|---|---|
| 100 | 15.59 | 15.38 | 15.59 | 15.33 | 15.47 | 0.14 | 0.88 | 73 | 27 |
| 50 | 15.67 | 15.53 | 15.43 | 15.48 | 15.53 | 0.10 | 0.67 | 62 | −24 |
| 25 | 15.78 | 15.68 | 16.07 | 15.95 | 15.87 | 0.17 | 1.09 | 27 | −9 |
| 5 | 17.21 | 17.05 | 17.07 | 17.10 | 17.11 | 0.07 | 0.41 | 5 | 3 |
| 1 | 19.02 | 18.88 | 18.88 | 18.79 | 18.89 | 0.10 | 0.51 | 1 | 4 |
| 0.2 | 20.80 | 20.59 | 20.45 | 20.18 | 20.51 | 0.26 | 1.26 | 0.222 | −11 |
| 0.04 | 22.38 | 22.02 | 21.58 | 21.43 | 21.85 | 0.43 | 1.98 | 0.034 | 15 |
| 0.008 | 21.99 | 21.59 | 22.91 | 22.81 | 22.33 | 0.64 | 2.87 | 0.009 | −12 |
| 0 | 23.96 | 24.32 | 23.83 | 23.56 | 23.92 | 0.32 | 1.32 | | |

TABLE 4 (B)

| Dilution | Ct Dup1A | Ct Dup1B | Ct Dup2A | Ct Dup2B | Ave Ct | SD | CV % | Observed nM | Observed nM × dilution factor |
|---|---|---|---|---|---|---|---|---|---|
| 1/100 | 20.08 | 20.02 | 19.68 | 19.62 | 19.85 | 0.23 | 1.17 | 0.4 | 41.7 |

Equivalents

Those skilled in the art will recognize, or be able to ascertain, using no more than routine experimentation, numerous equivalents to the specific embodiments described specifically herein. Such equivalents are intended to be encompassed in the scope of the following claims.

What is claimed is:

1. A method of detecting a target oligonucleotide in a sample, comprising the steps of:
   (a) contacting the sample with a first polynucleotide that is complementary to a first portion of the target oligonucleotide, so as to allow hybridization of the first polynucleotide with the target oligonucleotide, said first polynucleotide is joined to a tag, wherein the target oligonucleotide is an anti-VEGF aptamer having the structure:

(SEQ ID NO:1)
   PEG-linker-$C_fG_mG_mA_fA_fU_fC_fA_mG_mU_fG_mA_mA_mU_fG_mC_fU_fU_fA_m$
   $U_fA_mC_fA_mU_fC_fC_fG_m3'-3'-T_d$;

(b) contacting the sample with a second polynucleotide that is complementary to an adjacent and non-overlapping portion of the target oligonucleotide so as to allow hybridization of the second polynucleotide with the target oligonucleotide thereby forming a hybrid complex, said second polynucleotide comprises an amplifiable sequence that is substantially non-complementary to the target oligonucleotide; and
   (c) detecting the amplifiable sequence of the second polynucleotide in the hybrid complex by an amplification step, wherein the amplifiable sequence is detected using a fluorescent probe selected from the group consisting of a fluorescent probe comprising a nucleic acid having the sequence AAG GAA CTC TTC TGG AAT GA (SEQ ID NO: 8) and a fluorescent probe having the structure: 6FAM-AAG GAA CTC TTC TGG AAT GA-MGBNFQ (SEQ ID NO: 9),
   whereby, detection of the amplifiable sequence indicates that the target oligonucleotide is present in the sample.

2. The method of claim 1, further comprising the step of ligating the first polynucleotide and the second polynucleotide together, wherein the first polynucleotide and the second polynucleotide are hybridized adjacently to the target oligonucleotide, to form a ligated hybrid complex.

3. The method of claim 1, further comprising the step of separating the hybrid complex from the rest of the sample using the tag of the first polynucleotide.

4. The method of claim 1, wherein the tag is a high affinity ligand or binding partner thereto, wherein the high affinity ligand or binding partner thereto is selected from the group consisting of a hapten, an antibody, a ligand, a ligand-specific receptor, a carbohydrate, a carbohydrate-binding lectin, a biotin, an avidin, and a streptavidin.

5. The method of claim 1, wherein the tag is a magnetic bead.

6. The method of claim 1, wherein the first polynucleotide comprises the sequence AAAACGGATGTATAAGCA (SEQ ID NO: 3).

7. The method of claim 1, wherein the second polynucleotide comprises the sequence TTCACTGATTCCG (SEQ ID NO: 5).

8. A method of detecting a VEGF aptamer having the structure:

(SEQ ID NO:1)
   PEG-linker-$C_fG_mG_mA_fA_fU_fC_fA_mG_mU_fG_mA_mA_mU_fG_mC_fU_fU_fA_m$
   $U_fA_mC_fA_mU_fC_fC_fG_m3'-3'-T_d$, in a biological sample, comprising:
   (a) contacting the sample with a first polynucleotide that is complementary to a first portion of the VEGF aptamer to allow hybridization of the first polynucleotide with the VEGF aptamer, the first polynucleotide being joined to a tag and having the sequence: 5'-AAAACGGATG-TATAAGCA-3' (SEQ ID NO: 3);
   (b) contacting the sample with a second polynucleotide comprising the sequence TTCACTGATTCCG (SEQ ID NO: 5), that is complementary to an adjacent and non-overlapping portion of the VEGF aptamer to allow hybridization of the second polynucleotide with the VEGF aptamer, the second polynucleotide further comprising an amplifiable sequence that is substantially non-complementary to the VEGF aptamer;
   (c) ligating the first and the second polynucleotides together, wherein the first and second polynucleotides are hybridized adjacently to the VEGF aptamer, to form a ligated hybrid complex;
   (d) separating the ligated hybrid complex from the rest of the sample using the tag of the first polynucleotide; and (e) detecting the amplifiable sequence of the second polynucleotide by a polymerase chain reaction amplification using a fluorescent probe having the structure: 6FAM-AAG GAA CTC TTC TGG AAT GA-MGBNFQ (SEQ ID NO: 9), wherein the amplifiable sequence is detected when the VEGF aptamer is present in the biological sample, thereby detecting the VEGF aptamer in the biological sample.

9. A kit for detecting a target oligonucleotide in a sample, comprising:

(a) a first polynucleotide that is complementary to a first portion of the target oligonucleotide, so as to allow hybridization of the first polynucleotide with the target oligonucleotide, said first polynucleotide is joined to a tag, wherein the target oligonucleotide is an anti-VEGF aptamer having the structure:

(SEQ ID NO:1)
PEG-linker-$C_fG_mG_mA_fA_fU_fC_fA_mG_mU_fG_mA_mA_mU_fG_mC_fU_fU_fA_m$
$U_fA_mC_fA_mU_fC_fC_fG_m$3'-3'-$T_d$;

(b) a second polynucleotide that is complementary to an adjacent and non-overlapping portion of the target oligonucleotide so as to allow hybridization of the second polynucleotide with the target oligonucleotide, said second polynucleotide comprises an amplifiable sequence that is substantially non-complementary to the target oligonucleotide; and (c) a fluorescent probe comprising a nucleic acid complementary to at least a portion of the amplifiable sequence, wherein the fluorescent probe is selected from the group consisting of a fluorescent probe comprising a nucleic acid comprising the sequence AAG GAA CTC TTC TGG AAT GA (SEQ ID NO: 8) and a fluorescent probe having the structure: 6FAM-AAG GAA CTC TTC TGG AAT GA-MGBNFQ (SEQ ID NO: 9).

10. The kit of claim 9, wherein the tag is a high affinity ligand or binding partner thereto, wherein the high affinity ligand or binding partner thereto is selected from the group consisting of a hapten, an antibody, a ligand, a ligand-specific receptor, a carbohydrate, a carbohydrate-binding lectin, a biotin, an avidin, and a streptavidin.

11. The kit of claim 9, wherein the tag is a magnetic bead.

12. The kit of claim 9, wherein the first polynucleotide comprises the sequence AAAACGGATGTATAAGCA (SEQ ID NO: 3).

13. The kit of claim 9, wherein the second polynucleotide comprises the sequence TTCACTGATTCCG (SEQ ID NO: 5).

14. A method of detecting a target oligonucleotide in a sample, comprising the steps of:

(a) contacting the sample with a first polynucleotide that is complementary to a first portion of the target oligonucleotide, so as to allow hybridization of the first polynucleotide with the target oligonucleotide, said first polynucleotide is joined to a tag, wherein the first polynucleotide comprises the sequence AAAACGGATGTATAAGCA (SEQ ID NO: 3) and wherein the target oligonucleotide is an anti-VEGF aptamer having the structure:

(SEQ ID NO:1)
PEG-linker-$C_fG_mG_mA_fA_fU_fC_fA_mG_mU_fG_mA_mA_mU_fG_mC_fU_fU_fA_m$
$U_fA_mC_fA_mU_fC_fC_fG_m$3'-3'-$T_d$;

(b) contacting the sample with a second polynucleotide that is complementary to an adjacent and non-overlapping portion of the target oligonucleotide so as to allow hybridization of the second polynucleotide with the target oligonucleotide thereby forming a hybrid complex, said second polynucleotide comprises an amplifiable sequence that is substantially non-complementary to the target oligonucleotide; and (c) detecting the amplifiable sequence of the second polynucleotide in the hybrid complex by an amplification step, whereby, detection of the amplifiable sequence indicates that the target oligonucleotide is present in the sample.

15. The method of claim 14, further comprising the step of ligating the first polynucleotide and the second polynucleotide together, wherein the first polynucleotide and the second polynucleotide are hybridized adjacently to the target oligonucleotide, to form a ligated hybrid complex.

16. The method of claim 14, further comprising the step of separating the hybrid complex from the rest of the sample using the tag of the first polynucleotide.

17. The method of claim 14, wherein the tag is a high affinity ligand or binding partner thereto, wherein the high affinity ligand or binding partner thereto is selected from the group consisting of a hapten, an antibody, a ligand, a ligand-specific receptor, a carbohydrate, a carbohydrate-binding lectin, a biotin, an avidin, and a streptavidin.

18. The method of claim 14, wherein the tag is a magnetic bead.

19. The method of claim 14, wherein the amplifiable sequence is detected using a fluorescent probe.

20. The method of claim 19, wherein the fluorescent probe comprises a nucleic acid having the sequence AAG GAA CTC TTC TGG AAT GA (SEQ ID NO: 8).

21. The method of claim 19, wherein the fluorescent probe has the structure: 6FAM-AAG GAA CTC TTC TGG AAT GA-MGBNFQ (SEQ ID NO: 9).

22. The method of claim 14, wherein the second polynucleotide comprises the sequence TTCACTGATTCCG (SEQ ID NO: 5).

23. A method of detecting a target oligonucleotide in a sample, comprising the steps of:

(a) contacting the sample with a first polynucleotide that is complementary to a first portion of the target oligonucleotide, so as to allow hybridization of the first polynucleotide with the target oligonucleotide, said first polynucleotide is joined to a tag, wherein the target oligonucleotide is an anti-VEGF aptamer having the structure:

(SEQ ID NO:1)
PEG-linker-$C_fG_mG_mA_fA_fU_fC_fA_mG_mU_fG_mA_mA_mU_fG_mC_fU_fU_fA_m$
$U_fA_mC_fA_mU_fC_fC_fG_m$3'-3'-$T_d$;

(b) contacting the sample with a second polynucleotide that is complementary to an adjacent and non-overlapping portion of the target oligonucleotide so as to allow hybridization of the second polynucleotide with the target oligonucleotide thereby forming a hybrid complex, wherein the second polynucleotide comprises the sequence TTCACTGATTCCG (SEQ ID NO: 5) and wherein said second polynucleotide comprises an amplifiable sequence that is substantially non-complementary to the target oligonucleotide; and (c) detecting the amplifiable sequence of the second polynucleotide in the hybrid complex by an amplification step,
whereby, detection of the amplifiable sequence indicates that the target oligonucleotide is present in the sample.

24. The method of claim 23, further comprising the step of ligating the first polynucleotide and the second polynucleotide together, wherein the first polynucleotide and the second polynucleotide are hybridized adjacently to the target oligonucleotide, to form a ligated hybrid complex.

25. The method of claim 23, further comprising the step of separating the hybrid complex from the rest of the sample using the tag of the first polynucleotide.

26. The method of claim 23, wherein the tag is a high affinity ligand or binding partner thereto, wherein the high affinity ligand or binding partner thereto is selected from the group consisting of a hapten, an antibody, a ligand, a ligand-specific receptor, a carbohydrate, a carbohydrate-binding lectin, a biotin, an avidin, and a streptavidin.

27. The method of claim 23, wherein the tag is a magnetic bead.

28. The method of claim 23, wherein the amplifiable sequence is detected using a fluorescent probe.

29. The method of claim 28, wherein the fluorescent probe comprises a nucleic acid having the sequence AAG GAA CTC TTC TGG AAT GA (SEQ ID NO: 8).

30. The method of claim 28, wherein the fluorescent probe has the structure: 6FAM-AAG GAA CTC TTC TGG AAT GA-MGBNFQ (SEQ ID NO: 9).

31. The method of claim 28, wherein the first polynucleotide comprises the sequence AAAACGGATGTATAAGCA (SEQ ID NO: 3).

32. A kit for detecting a target oligonucleotide in a sample, comprising:
(a) a first polynucleotide that is complementary to a first portion of the target oligonucleotide, so as to allow hybridization of the first polynucleotide with the target oligonucleotide, wherein the first polynucleotide comprises the sequence AAAACGGATGTATAAGCA (SEQ ID NO: 3), wherein said first polynucleotide is joined to a tag, and wherein the target oligonucleotide is an anti-VEGF aptamer having the structure:

(SEQ ID NO:1)
PEG-linker-$C_fG_mG_mA_rA_rU_fC_fA_mG_mU_fG_mA_mA_mU_fG_mC_fU_fU_fA_m$
$U_fA_mC_fA_mU_fC_fC_fG_m3'$-$3'$-$T_d$;

(b) a second polynucleotide that is complementary to an adjacent and non-overlapping portion of the target oligonucleotide so as to allow hybridization of the second polynucleotide with the target oligonucleotide, said second polynucleotide comprises an amplifiable sequence that is substantially non-complementary to the target oligonucleotide; and
(c) a fluorescent probe comprising a nucleic acid complementary to at least a portion of the amplifiable sequence.

33. The kit of claim 32, wherein the tag is a high affinity ligand or binding partner thereto, wherein the high affinity ligand or binding partner thereto is selected from the group consisting of a hapten, an antibody, a ligand, a ligand-specific receptor, a carbohydrate, a carbohydrate-binding lectin, a biotin, an avidin, and a streptavidin.

34. The kit of claim 32, wherein the tag is a magnetic bead.

35. The kit of claim 32, wherein the fluorescent probe comprises a nucleic acid comprising the sequence AAG GAA CTC TTC TGG AAT GA (SEQ ID NO: 8).

36. The kit of claim 32, wherein the fluorescent probe has the structure: 6FAM-AAG GAA CTC TTC TGG AAT GA-MGBNFQ (SEQ ID NO: 9).

37. The kit of claim 32, wherein the second polynucleotide comprises the sequence TTCACTGATTCCG (SEQ ID NO: 5).

38. A kit for detecting a target oligonucleotide in a sample, comprising:
(a) a first polynucleotide that is complementary to a first portion of the target oligonucleotide, so as to allow hybridization of the first polynucleotide with the target oligonucleotide, said first polynucleotide is joined to a tag, wherein the target oligonucleotide is an anti-VEGF aptamer having the structure:

(SEQ ID NO:1)
PEG-linker-$C_fG_mG_mA_rA_rU_fC_fA_mG_mU_fG_mA_mA_mU_fG_mC_fU_fU_fA_m$
$U_fA_mC_fA_mU_fC_fC_fG_m3'$-$3'$-$T_d$;

(b) a second polynucleotide that is complementary to an adjacent and non-overlapping portion of the target oligonucleotide so as to allow hybridization of the second polynucleotide with the target oligonucleotide, wherein the second polynucleotide comprises the sequence TTCACTGATTCCG (SEQ ID NO: 5), and wherein said second polynucleotide comprises an amplifiable sequence that is substantially non-complementary to the target oligonucleotide; and
(c) a fluorescent probe comprising a nucleic acid complementary to at least a portion of the amplifiable sequence.

39. The kit of claim 38, wherein the tag is a high affinity ligand or binding partner thereto, wherein the high affinity ligand or binding partner thereto is selected from the group consisting of a hapten, an antibody, a ligand, a ligand-specific receptor, a carbohydrate, a carbohydrate-binding lectin, a biotin, an avidin, and a streptavidin.

40. The kit of claim 38, wherein the tag is a magnetic bead.

41. The kit of claim 38, wherein the fluorescent probe comprises a nucleic acid comprising the sequence AAG GAA CTC TTC TGG AAT GA (SEQ ID NO: 8).

42. The kit of claim 38, wherein the fluorescent probe has the structure: 6FAM-AAG GAA CTC TTC TGG AAT GA-MGBNFQ (SEQ ID NO: 9).

43. The kit of claim 38, wherein the first polynucleotide comprises the sequence AAAACGGATGTATAAGCA (SEQ ID NO: 3).

* * * * *